United States Patent
Woodacre et al.

(10) Patent No.: US 11,806,553 B2
(45) Date of Patent: Nov. 7, 2023

(54) TRANSDUCER ASSEMBLY FOR GENERATING FOCUSED ULTRASOUND

(71) Applicant: DALHOUSIE UNIVERSITY, Halifax (CA)

(72) Inventors: Jeffrey Kyle Woodacre, Halifax (CA); Jeremy Brown, Halifax (CA)

(73) Assignee: DALHOUSIE UNIVERSITY, Halifax (CA)

(*) Notice: Subject to any disclaimer, the term of this patent is extended or adjusted under 35 U.S.C. 154(b) by 363 days.

(21) Appl. No.: 16/642,603

(22) PCT Filed: Aug. 30, 2018

(86) PCT No.: PCT/CA2018/051047
§ 371 (c)(1),
(2) Date: Feb. 27, 2020

(87) PCT Pub. No.: WO2019/041040
PCT Pub. Date: Mar. 7, 2019

(65) Prior Publication Data
US 2020/0346044 A1 Nov. 5, 2020

Related U.S. Application Data

(60) Provisional application No. 62/629,475, filed on Feb. 12, 2018, provisional application No. 62/553,719, filed on Sep. 1, 2017.

(51) Int. Cl.
*A61N 7/00* (2006.01)

(52) U.S. Cl.
CPC .......... *A61N 7/00* (2013.01); *A61N 2007/003* (2013.01); *A61N 2007/006* (2013.01);
(Continued)

(58) Field of Classification Search
CPC ................ A61N 7/00; A61N 2007/003; A61N 2007/0039; A61N 2007/006;
(Continued)

(56) References Cited

U.S. PATENT DOCUMENTS 3,663,842 A 5/1972 Miller
4,477,783 A * 10/1984 Glenn .................. B06B 1/0611
333/147

(Continued)

FOREIGN PATENT DOCUMENTS

WO 2009094554 A3 7/2009
WO 2016210133 A1 12/2016

OTHER PUBLICATIONS

Why Does an Ultrasound Probe Need Matching Layers (Year: 2017).*

(Continued)

*Primary Examiner* — Hien N Nguyen
(74) *Attorney, Agent, or Firm* — HILL & SCHUMACHER

(57) ABSTRACT

Systems and devices are provided for generating focused ultrasound pulses based on a transducer assembly having a piezoelectric layer coupled to an acoustic lens. In some example embodiments, the piezoelectric layer is a composite piezoelectric material having an acoustic impedance configured to match the acoustic impedance of the acoustic lens. The acoustic lens may be formed from aluminum, or an alloy thereof, and may have a distal surface having a non-spherical profile for producing a focal region that is smaller than an equivalent spherical lens. The acoustic lens may have an f-number less than unity. In some embodiments, the acoustic lens is coated with a polymer acoustic impedance matching layer that is compatible with deposition via chemical vapor deposition, such as a p-xylylene based polymer. In some embodiments, the acoustic lens is formed
(Continued)

from aluminum or an alloy thereof, and the polymer acoustic impedance matching layer is a Parylene layer.

29 Claims, 23 Drawing Sheets

(52) U.S. Cl.
CPC ............... *A61N 2007/0039* (2013.01); *A61N 2007/0082* (2013.01)

(58) Field of Classification Search
CPC .... A61N 2007/0082; A61N 2007/0065; A61N 7/02; A61B 17/225; B06B 1/067
See application file for complete search history.

(56) References Cited

U.S. PATENT DOCUMENTS

| | | | | |
|---|---|---|---|---|
| 4,945,915 | A * | 8/1990 | Nagasaki | G01S 15/8913 600/443 |
| 10,325,768 | B1 * | 6/2019 | Stearns | H01J 49/0445 |
| 2007/0055183 | A1 | 3/2007 | Kaminski et al. | |
| 2007/0083120 | A1 | 4/2007 | Cain et al. | |
| 2008/0195003 | A1 | 8/2008 | Sliwa et al. | |
| 2008/0284820 | A1 * | 11/2008 | Pan | B41J 2/16 347/46 |
| 2011/0054363 | A1 | 3/2011 | Cain et al. | |
| 2013/0190623 | A1 | 7/2013 | Bertolina et al. | |
| 2013/0289593 | A1 * | 10/2013 | Hall | H01L 41/04 264/109 |
| 2014/0100459 | A1 | 4/2014 | Xu et al. | |
| 2014/0180102 | A1 | 6/2014 | Sinelnokov | |
| 2014/0180128 | A1 * | 6/2014 | Corl | A61B 6/461 600/467 |
| 2016/0287909 | A1 | 10/2016 | Maxwell et al. | |
| 2017/0000376 | A1 | 1/2017 | Partanen et al. | |
| 2017/0156691 | A1 * | 6/2017 | Cabrera-Munoz | A61B 8/461 |
| 2017/0263846 | A1 * | 9/2017 | Nakamura | H01L 41/0825 |

OTHER PUBLICATIONS

Lin et al., IEEE Trans Ultrason Ferroelectr Freq Control, 61, 251-265, 2014.
International Search Report dated Dec. 27, 2018, of the parent PCT application PCT/CA2018/051047 filed Aug. 30, 2018.

* cited by examiner

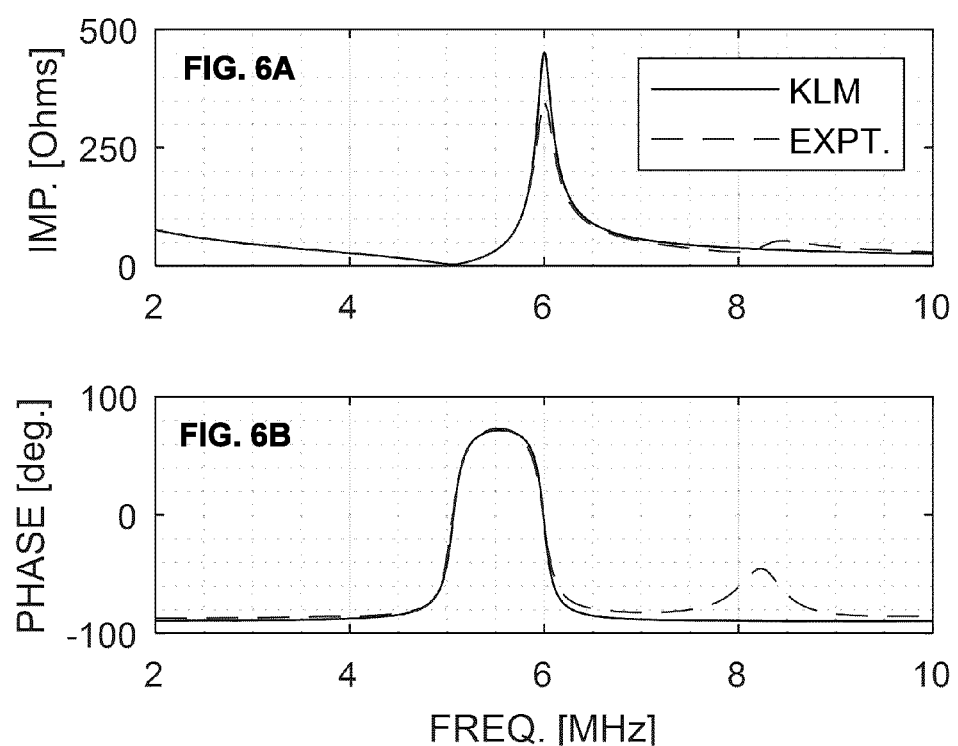

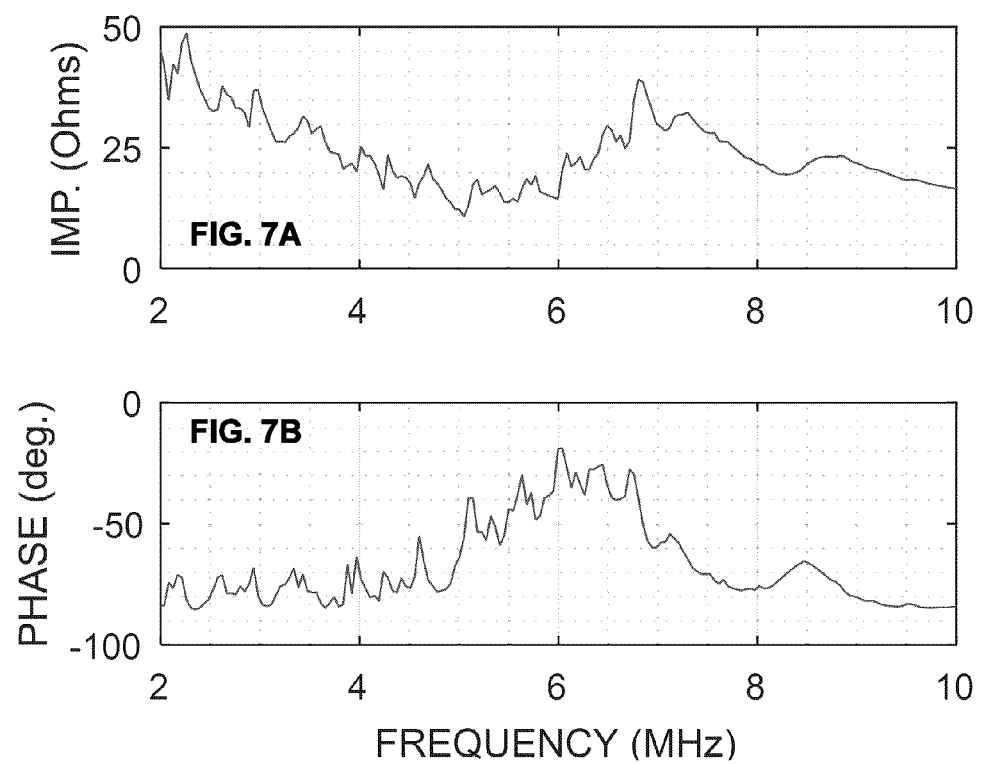

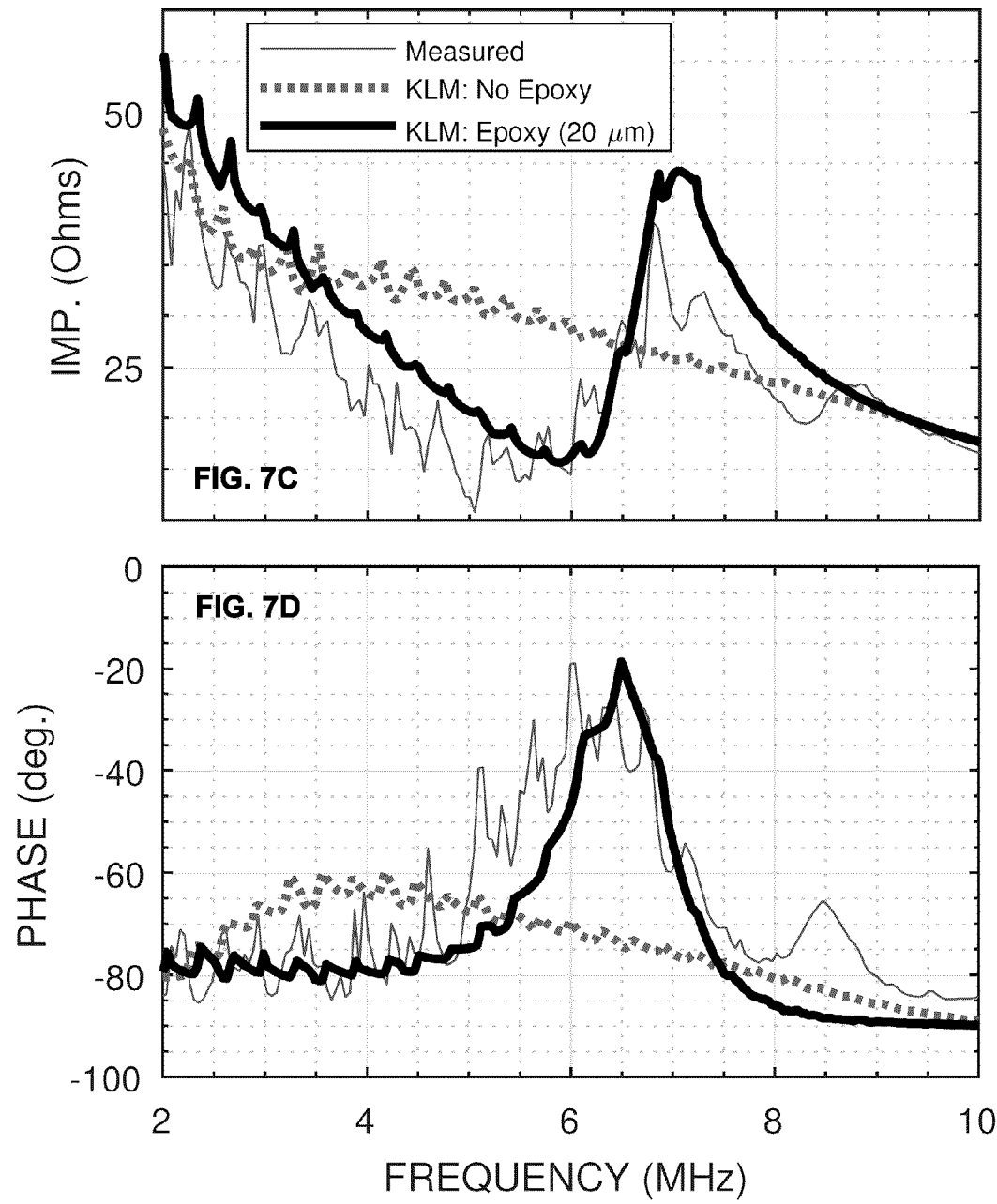

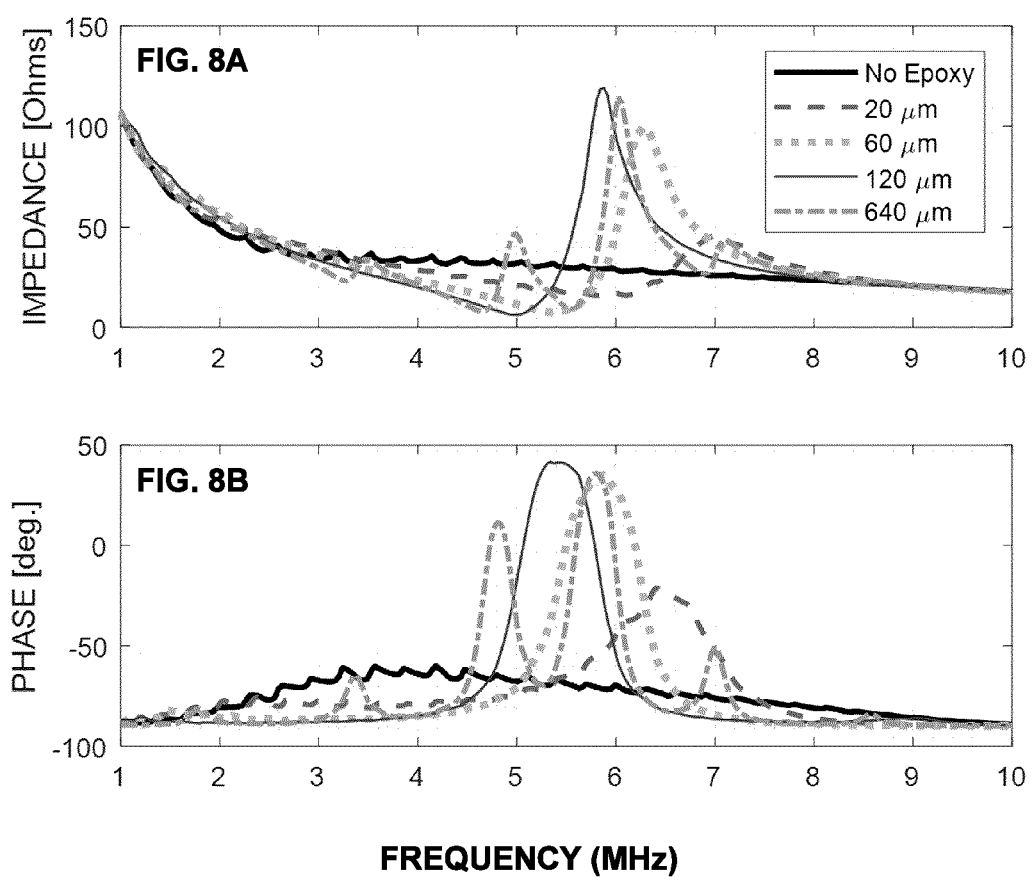

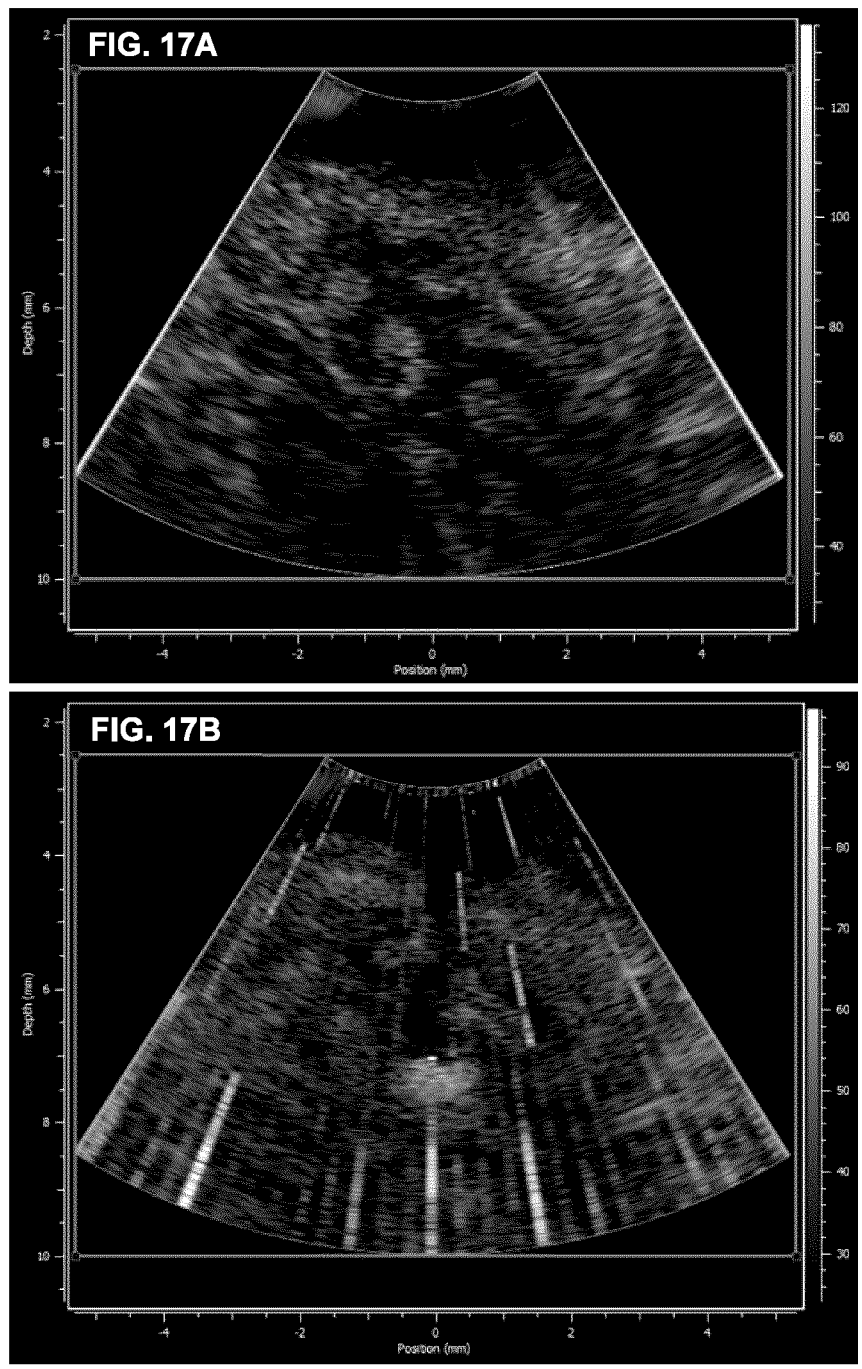

TRANSDUCER ASSEMBLY FOR GENERATING FOCUSED ULTRASOUND

CROSS-REFERENCE TO RELATED APPLICATION

This application is a National Phase application claiming the benefit of the international PCT Patent Application No. PCT/CA2018/051047, filed on Aug. 30, 2018 in English, which claims priority to U.S. Provisional Application No. 62/553,719, titled "TRANSDUCER ASSEMBLY FOR GENERATING FOCUSED ULTRASOUND" and filed on Sep. 1, 2017, the entire contents of which are incorporated herein by reference, and to U.S. Provisional Application No. 62/629,475, titled "TRANSDUCER ASSEMBLY FOR GENERATING FOCUSED ULTRASOUND" and filed on Feb. 12, 2018, the entire contents of which is incorporated herein by reference.

BACKGROUND

The present disclosure relates to focused ultrasound. In particular, the present disclosure relates to focused ultrasound for therapeutic applications, such as histotripsy and high intensity focused ultrasound (HIFU).

Histotripsy is a tissue ablation process in which short bursts of high intensity ultrasound are focused to a small focal region, exceeding the vapor pressure within the focal region and causing gas bubbles to form. When these bubbles collapse, the shockwave destroys the tissue structure, leaving liquified remnants of the original tissue at the focal region. HIFU (High-intensity focused ultrasound) provides another ultrasound-based tissue ablation method in which ultrasound is focused to small focal region, but with relatively long and sustained waves, increasing the temperature within the focal region until tissue is thermally destroyed. As HIFU is a thermal process, heat can also damage the surrounding tissue. Both HIFU and histotripsy transducers function similarly, as both require the focusing of ultrasound to a small focal region.

SUMMARY

Systems and devices are provided for generating focused ultrasound pulses based on a transducer assembly having a piezoelectric layer coupled to an acoustic lens. In some example embodiments, the piezoelectric layer is a composite piezoelectric material having an acoustic impedance configured to match the acoustic impedance of the acoustic lens. The acoustic lens may be formed from aluminum, or an alloy thereof, and may have a distal surface having a non-spherical profile for producing a focal region that is smaller than an equivalent spherical lens. The acoustic lens may have an f-number less than two. In some embodiments, the acoustic lens is coated with a polymer acoustic impedance matching layer that is compatible with deposition via chemical vapor deposition, such as a p-xylylene based polymer. In some embodiments, the acoustic lens is formed from aluminum or an alloy thereof, and the polymer acoustic impedance matching layer is a Parylene layer.

Accordingly, in one aspect, there is provided an ultrasound transducer assembly for generating focused ultrasound, the ultrasound transducer assembly comprising:
a piezoelectric layer;
an acoustic lens having a proximal surface and a curved distal surface, wherein the proximal surface is attached to the piezoelectric layer; and
an acoustic impedance matching layer coating the curved distal surface of the acoustic lens;
wherein an acoustic impedance of the piezoelectric layer approximately matches an acoustic impedance of the acoustic lens.

In another aspect, there is provided an ultrasound transducer assembly for generating focused ultrasound, the ultrasound transducer assembly comprising:
a composite piezoelectric layer;
an acoustic lens having a proximal surface and a curved distal surface, wherein the proximal surface is attached to the composite piezoelectric layer, wherein the acoustic lens comprises 85% aluminum by weight; and
a polymer acoustic impedance matching layer coating the curved distal surface of the acoustic lens, wherein the polymer acoustic impedance matching layer is formed from a p-xylylene based polymer;
wherein an acoustic impedance of the composite piezoelectric layer matches an acoustic impedance of the acoustic lens within +−40%; and
wherein the curved distal surface has an elliptical shape; and
wherein the acoustic lens has an f-number of less than two.

In another aspect, there is provided an ultrasound system for generating focused ultrasound, the ultrasound system comprising:
an ultrasound transducer assembly comprising:
a piezoelectric layer;
an acoustic lens having a proximal surface and a curved distal surface, wherein the proximal surface is attached to the piezoelectric layer; and
an acoustic impedance matching layer coating the curved distal surface of the acoustic lens;
driver circuitry operably connected with the ultrasound transducer assembly, wherein the driver circuitry is configured to deliver electrical pulses with a voltage and operating frequency sufficient for generating ultrasound pulses for performing histotripsy;
wherein an acoustic impedance of the piezoelectric layer approximately matches an acoustic impedance of the acoustic lens; and
wherein the acoustic impedance matching layer is a quarter wave matching layer.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 6A and 6B plot, respectively, the measured electrical impedance and phase of an example transducer composite without a lens attached, shown results from simulations employing a KLM model, illustrating the close correspondence between the measured and simulated results. The resonance peak from FIGS. 6A and 6B are observed to spread over the spectrum due to the presence of the lens.

FIGS. 7A and 7B plot impedance and phase measurements for a composite transducer assembly having an integrated acoustic lens.

FIG. 7C shows the electrical impedance magnitude of composite-lens stack along with KLM models both with and without the bonding epoxy between composite and lens. Modelling the bonding epoxy is necessary to ensure the KLM resonance matches the measured resonance. Discrepancies are likely due to the inability of KLM to model internal lens reflections.

FIG. 7D shows the electrical impedance phase where, again, the addition of 20 μm of epoxy allows KLM to more closely match the phase characteristics.

FIGS. 8A and 8B plot KLM model impedance spectra for transducers with 0, 20, 60, 120, and 640 micrometer epoxy layers, where (A) plots the impedance magnitude and (B) plots the impedance phase. A quarter wavelength matching layer was included for each respective epoxy layer thickness.

FIGS. 17A and 17B show (A) a chinchilla cerebellum imaged showing the molecular layer (dark layer), the granular layer (highly specular), and white matter tracts (thin dark lines in granular layer) and (B) a histotripsy bubble cloud, visible as a highly specular region near the image center, has been plunged into the cerebellum. Both images were collected in real-time using a co-registered 40 MHz endoscopic phased array.

DETAILED DESCRIPTION

Figure 1:
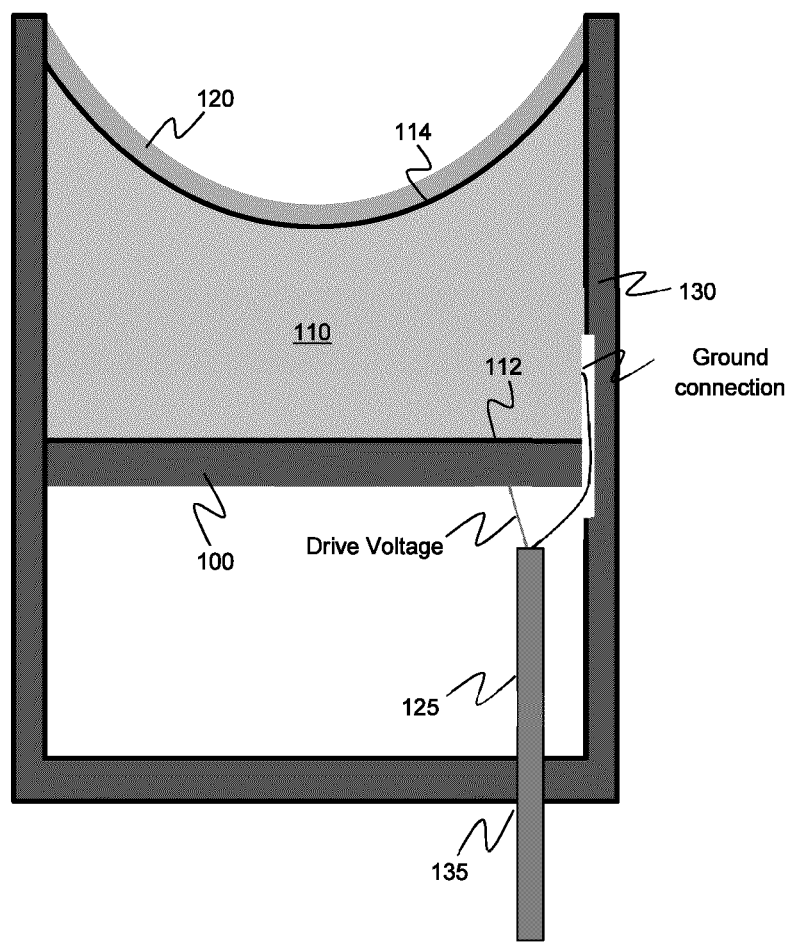
FIG. 1 shows an example transducer assembly for generating therapeutic focused ultrasound, in which a piezoelectric layer is coupled to an acoustic lens.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrase "co-registered", when employed with reference to the relationship between a therapeutic ultrasound transducer and an imaging ultrasound transducer, refers to a fixed mechanical relationship between the therapeutic ultrasound transducer and the imaging ultrasound transducer, where a focal region of the therapeutic ultrasound transducer lies within an imaging region of the imaging ultrasound transducer.

Various embodiments of the present disclosure provide systems and devices for generating therapeutic focused ultrasound, for example, for therapeutic applications such as tissue ablation.

The example embodiments described herein arose from technical solutions that were discovered when addressing technical problems encountered when attempting to fabricated curved piezoelectric materials for use in histotripsy applications. The present inventors initially fabricated histotripsy transducers from a 1-3 connected composite (made of piezoelectric pillars interspersed in a matrix of epoxy). Soft epoxies were employed, permitting the bending of the composite to facilitate focusing to some degree. However, during experimentation with a number of epoxies, it was found that soft epoxies curved well, but failed to hold their shape and were not capable of providing an appropriate composite thickness to achieve a desired control over transducer frequency. It was also found that if the epoxy was too hard, the desirable composite thickness could be achieved, but the composite would crack and break when attempting to curve into the composite into the shape needed to achieve sufficient focusing for histotripsy applications. These approaches were therefore found to lead to manufacturing challenges that resulted in low device yield and high device cost.

The present inventors, seeking a solution to this problem, employed an alternative design involving the use of an acoustic lens formed in a passive material that is attached to an active piezoelectric composite substrate. An example of such an embodiment is illustrated in FIG. 1. As shown in the figure, the transducer assembly includes a piezoelectric layer 100 that is attached to an acoustic lens 110 at a proximal surface 112 thereof. The distal surface 114 of the acoustic lens is coated with a polymer impedance matching layer 120 having a thickness (e.g. λ/4) and acoustic impedance suitable for impedance matching between the acoustic impedance of the acoustic lens 110 and the acoustic impedance of tissue (e.g. the acoustic impedance of water).

In some example embodiments, the distal surface of the piezoelectric layer 100 may be adhered to the proximal surface 112 of the acoustic lens 110 using a thin layer of adhesive, such as a thin layer of epoxy. The thickness of the epoxy may be selected to be less than the wavelength associated with the operating frequency of the ultrasound transducer assembly to ensure good transmission acoustic energy into the acoustic lens 110.

As shown in the examples below, when modelling the impedance of transducers having an intermediate layer (such as an intermediate bonding layer that may be formed from epoxy or another adhesive) between the piezoelectric layer 100 and the acoustic lens 110, it was found that the acoustic properties of the intermediate layer needed to be considered in the simulations in order to achieve suitable agreement between the simulated impedance spectrum and the experimentally measured impedance spectrum.

Indeed, as explained in detail in the examples below, it was found that the acoustic power transfer of a transducer having an acoustic lens bonded to a piezoelectric material via an epoxy layer was dependent on the epoxy thickness. For example, simulations demonstrated that as the thickness of the epoxy layer is increased, the power transfer of device increases, albeit with reduced efficiency and bandwidth, as well as a frequency shift of the resonance, provided that the acoustic impedance of the epoxy layer is lower than that of the acoustic lens and piezoelectric layer.

Accordingly, in some example embodiments, an intermediate layer may be provided between the acoustic lens and the piezoelectric layer, where the acoustic impedance of the intermediate layer is lower than the respective acoustic impedances of the acoustic lens and the piezoelectric layer, and wherein the thickness of the intermediate layer is selected to control or achieve one or more device performance parameters, such as, but not limited to, power transfer, emission bandwidth, and resonant frequency. For example, the thickness of the intermediate layer may be selected to modify or select the transducer output power for a given input power, where, for example, increasing film thickness may provide improved acoustic power output for a given input voltage relative to a case with a thin (<20 µm) intermediate layer. It will be understood that in the present example embodiment in which the thickness of the intermediate layer is selected to control or obtain one or more device properties, the intermediate layer may be electrically conductive or non-conductive. In some example implementations, the intermediate layer may have a thickness between 15 and 25 microns, or a thickness between 15 and 50 microns, or a thickness between 20 and 50 microns, or a thickness between 25 and 50 microns, or a thickness between 50 and 70 microns, or a thickness between 50 and 100 microns, or a thickness between 50 and 150 microns, or a thickness between 100 and 150 microns, or a thickness between 100 and 200 microns, or a thickness of at least 15 microns, or a thickness of at least 20 microns, or a thickness of at least 50 microns, or a thickness of at least 75 microns, or a thickness of at least 100 microns.

Although many of the examples provided below employ epoxy as the material forming an intermediate layer between the acoustic lens and the piezoelectric layer, it will be understood that the intermediate layer may be formed from a wide variety of materials. In some example embodiments, the intermediate layer may be formed from an adhesive, such as an epoxy or glue. In other example embodiments, the intermediate layer may be a material other than an adhesive, such as a liquid layer, for example, oil or water.

In some example embodiments, the matching layer 120 may be a quarter wave matching layer corresponding to the frequency associated with the peak in the acoustic power spectrum of the transducer assembly, where the frequency of the peak is dependent on the thickness of the intermediate layer. Additionally or alternatively, the drive frequency of the transducer assembly may correspond to (e.g. coincide with, or lie within a 3 dB bandwidth) the frequency associated with a peak in the acoustic power spectrum of the transducer assembly, where the frequency of the peak is dependent on the thickness of the intermediate layer. In some example implementations, the thickness of the intermediate layer may be selected to be sufficient to effect an increase in peak emitted acoustic power in the acoustic power spectrum of the ultrasound transducer assembly by at least two or three relative to an equivalent ultrasound transducer assembly absent of the intermediate layer (as may be determined, for example, via experimentation and/or simulation). In some example implementations, the thickness of the intermediate layer may be selected to be sufficient to effect an increase in peak efficiency in an acoustic efficiency spectrum of the ultrasound transducer assembly by at least 20% or 40% relative to an equivalent ultrasound transducer assembly absent of the intermediate layer.

It will be understood that the modification or selection of device properties based on the thickness of an intermediate layer need not be limited to lensed transducers (transducers having a fixed focus via a geometric lens). Accordingly, in some example embodiments, an intermediate layer may be provided between a piezoelectric material and a second material to increase the overall power transfer from the piezoelectric to the second material for a given drive voltage of the piezoelectric, while additionally shifting the drive frequency at which maximum output power occurs, where the magnitude of this shift depends on layer thickness, where the acoustic impedance of the intermediate layer is lower than the acoustic impedances of the piezoelectric material and the second material. It is expected that the preceding example embodiments in which epoxy properties are selected to improve power output will have benefits in the design of both HIFU and histotripsy transducers, in which a lower drive voltage and therefore less complex electronics will be needed for treatments. The cost of this increased power output is a reduced bandwidth, which may affect the effectiveness or efficiency of histotripsy, as some histotripsy treatments are more highly targetable with a short-duration, wide-bandwidth pulse. The example embodiment of FIG. 1 shows an example of a non-limiting implementation of a housing 130 for mechanically supporting the piezoelectric layer 100 and the acoustic lens 110. As shown in the figure, the acoustic lens 110 and the piezoelectric layer 100 may be recessed within a housing 130 that is non-conductive. Electrical cabling 125 (e.g. a coaxial cable) enters the housing 130 through a hole or aperture 135 (e.g. which may be sealed with a water-resistant epoxy, adhesive or other sealing material), and electrical connections are made within the housing 130 between the drive and ground wires and respective surfaces of the piezoelectric layer 100.

In the example embodiment illustrated in FIG. 1, air backing is employed to ensure that the acoustic energy emerges from the front of the device and into the tissue. However, it will be understood that other backing materials could be used in the alternative, albeit with a reduction in the device output.

FIG. 1 illustrates a non-limiting example embodiment in which the acoustic lens 110 is electrically conductive, where the ground connection to the distal surface of the piezoelectric layer 100 is made indirectly through the conductive acoustic lens 110, and through a conductive adhesive layer that attaches the piezoelectric layer 100 to the acoustic lens 110. The ground connection may be connected to the acoustic lens 110, for example, via conductive epoxy or simply via contacted under the application of pressure (e.g. using a spring or set screw; not shown).

During the design and the experimental and simulated characterization of the transducer assembly, the present inventors found that in order to achieve sufficient focusing for generating and sustaining a bubble cloud for histotripsy applications, the conventional approach involving a circular lens shape was insufficient, as spherical aberrations hampered the ability to achieve a sufficiently small focus. In order to address this problem, the present inventors adapted the design such that the outer curved surface of the acoustic lens is non-spherical, thereby avoiding spherical aberrations and facilitating a tighter focus than that achievable with a lens having a spherical surface. In some example embodiments, an elliptical lens surface was selected in order to achieve improved focusing.

Furthermore, the inventors found that it is beneficial for the acoustic lens to have a low f-number, such as an f-number of less than one (unity), or an f-number less than two, in order to facilitate the generation of a sufficiently strong focus for histotripsy applications. The inventors selected aluminum (or alloys thereof, e.g. a metal alloy containing at least 85% aluminum by weight) as a suitable material for the acoustic lens, since aluminum is a low-cost material that could be readily machined (e.g. using CNC machining) in order to achieve the high curvature needed to a produce a low-f-number acoustic lens, and to achieve the non-spherical (e.g. elliptical) shape that facilitates strong focusing.

In some example embodiments, the curvature of the lens is elliptical and can be described using the following equation, derived from Fermat's Theorem:

$$y^2 = x^2\left[\left(\frac{v_m}{v_l}\right)^2 + 1\right] + 2r_f x\left(1 - \frac{v_m}{v_l}\right)$$

where x and y are Cartesian coordinates for the curve, $v_m$ and $v_l$ are the longitudinal wave speed in the ablation medium and lens, respectively, and $r_f$ is the focal distance from the center of the lens curvature (x=0 and y=0), or focal radius. The elliptical lens shape avoids spherical aberrations in the lens, which are important to avoid when the lens focus is smaller than the lens aperture.

Having selected a suitable material for machining the desired curvature of the acoustic lens, the inventors then considered the acoustic impedances of the piezoelectric layer 100, the acoustic lens 110, and the polymer acoustic impedance matching layer 120. Aluminum has an acoustic impedance of approximately 17 MRayls, which is significantly lower than conventional piezoelectric materials. The piezoelectric layer 100 was therefore configured as a piezoelectric composite with a volume fraction of piezoelectric material selected to achieve or approximate acoustic impedance matching between the piezoelectric layer 100 and the acoustic lens 110. It will be understood that the acoustic impedance of the piezoelectric layer approximately matches the acoustic impedance of the acoustic lens when the acoustic impedance of the piezoelectric layer is within ±40% of the acoustic impedance of the acoustic lens.

For example, as described in the Examples section below, a composite piezoelectric layer may be formed as a 1-3 piezoelectric composite having a volume fraction and pillar geometry suitable to achieve or approximate the impedance matching condition, with an acoustic impedance equal to, or approximately equal to, 17 MRayls. For example, the acoustic impedance of the composite piezoelectric layer may lie between 16 and 18 MRayls, between 15 and 19 MRayls, between 14 and 20 MRayls, or between 13 and 21 MRayls. Such an acoustic impedance matches (or approximately matches) the acoustic impedance of the aluminum lens, ensuring that a substantial fraction of the acoustic energy outputted by the composite is transferred into the acoustic lens.

It will be understood that the piezoelectric composite need not have a 1-3 configuration, and other composites, such as a 2-2 composite, may be employed in the alternative. While some of the example implementations described herein involve the use of a composite piezoelectric layer, it will be understood that other example implementations may involve non-composite piezoelectric layers.

According to various non-limiting example implementations, the composite could be made from any form of piezoelectric ceramic (e.g. PZT-4, PZT-5A, PZT-5H, PMN-PT), although the choice of ceramic will affect the drive voltage necessary to perform histotripsy as well as the saturation voltage at which driving the piezoelectric harder no longer increases pressure output. Single-crystal PMN-PT piezoelectric could also be used.

The present inventors also discovered that by selecting an p-xylylene based polymer for the polymer impedance matching layer 120, efficient impedance matching could be achieved between the aluminum acoustic lens 110 and tissue (or a propagation medium having an acoustic impedance approximately equal to that of tissue or water). Indeed, in one example implementation, Parylene C was selected as a suitable polymer for forming the polymer impedance matching layer 120. As the acoustic impedance of Parylene C is approximately 2.7 MRayl, this acoustic impedance is close to the target acoustic impedance that is predicted by the following acoustic impedance matching equation for a single λ/4 impedance matching layer:

$$Z_m = \sqrt[3]{Z_1 Z_2^2} \sim 3.3 \text{ MRayls}$$

where $Z_1$ is the impedance of aluminum (~17 MRayls) and $Z_2$ is the acoustic impedance of water (~1.5 MRayls). In other example implementations, other types of p-xylylene based polymers may alternatively be employed, such as Parylene N or Parylene D.

The use of an p-xylylene based polymer for the acoustic impedance matching layer 120 is beneficial in that it is compatible with chemical vapor deposition (CVD). CVD is particularly beneficial in the context of example embodiments involving the formation of an acoustic impedance matching layer on the highly curved surface of low (e.g. sub-unity, or less than two) f-number acoustic lens, because CVD can achieve a uniform coating thickness even in the presence of high curvature. Moreover, existing commercially-available CVD deposition equipment is compatible with Parylene deposition with layer thicknesses suitable for forming an λ/4 layer for frequencies suitable for histotripsy applications.

Although much of the present disclosure provides example implementations in which the polymer impedance matching layer is formed from Parylene C, it will be understood that other types of polymers may be used. For example, in some example implementations, other CVD-compatible polymers, having acoustic impedances in the range of 2.5-4 MRayls, may be alternatively employed, such as polyimide or fluoropolymers such as Teflon.

Although aluminum (or an aluminum alloy) is preferable as a material for the acoustic lens when combined with an p-xylylene based polymer acoustic impedance matching layer, a glass-based material may alternatively be employed for the acoustic lens in order to achieve a suitable set of materials for acoustic impedance matching or approximate impedance matching. For example, glasses such as quartz glass and silica glass have acoustic impedance values in the range of 13-15 MRayls.

As described above, applications involving histotripsy benefit from an acoustic lens having a low f-number, such as, in one example embodiment, an f-number less than unity, or in another example embodiment, an f-number less than two. Beam width and depth-of-field for the therapeutic focused transducer are linearly and quadratically proportional to f-number (F #) respectively, so increasing F # causes the size of the focus and, therefore, the volume over which the ultrasound energy is spread, to increase, requiring a higher drive voltage to the transducer to reach cavitation pressures. Also, since the focus is less tight with increasing F #, the ability to target ablation to specific areas diminishes. When a low F # lens is employed, such as an F # less than unity, or an F # less than two, the use of a non-spherical lens (such as an elliptical lens) avoids spherical aberrations, which occur with such tightly focused lenses. Such spherical aberrations would otherwise result in a larger effective focal area, and would also reduce the pressure within the focal region and require higher drive voltages.

Figure 2:
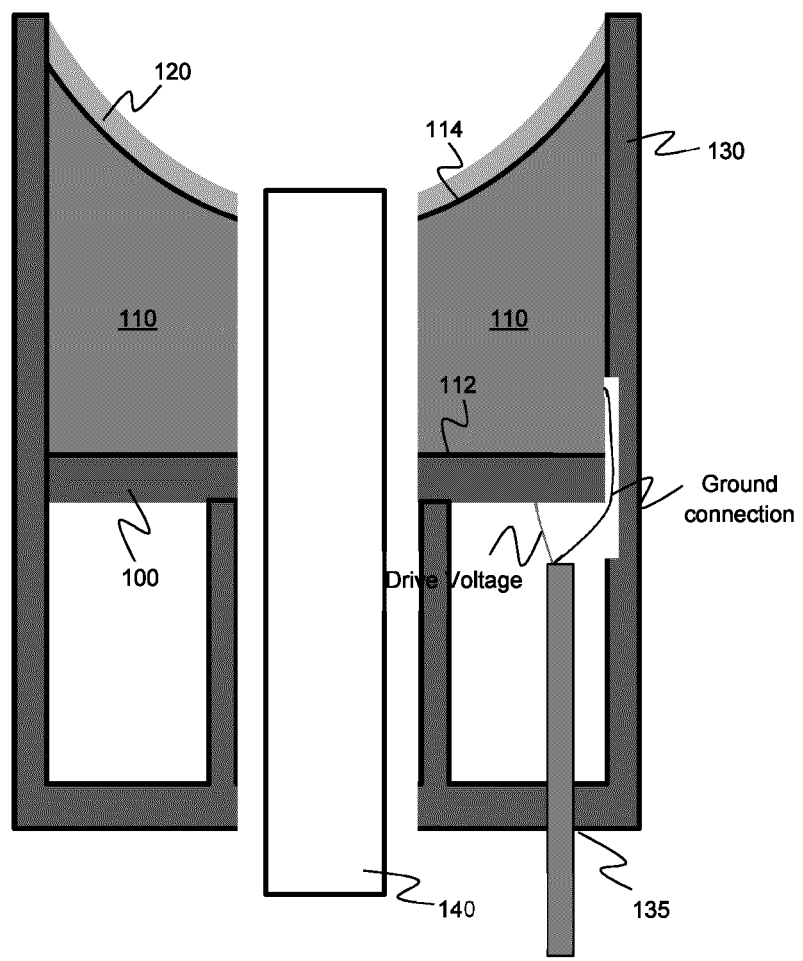
FIG. 2 shows an example transducer assembly in which a piezoelectric layer is coupled to an acoustic lens for generating and therapeutic focused ultrasound, and where the transducer assembly includes a coaxial imaging transducer for co-registered imaging and ultrasound therapy.

Referring now to FIG. 2, an alternative example embodiment is illustrated in which the transducer assembly includes a co-registered imaging transducer. In the example embodiment shown, the imaging transducer 140 is received and housed in a coaxial manner relative to the acoustic lens 110, with the distal end of the imaging transducer emerging through an aperture formed in the distal surface of the acoustic lens 110. In some example applications, the imaging transducer is a miniaturized endoscopic transducer, e.g. having a diameter less than 4 mm, permitting the housing of the imaging transducer within an acoustic lens having a diameter less than 10 mm.

The imaging transducer may be supported within the transducer assembly according to a wide range of example implementations, and a specific method may depend on the device geometry. In the example case of an endoscopic phased array imaging transducer, set screws may be provided in the housing that gently press into the phased array device, supporting it in place, in a removable fashion. Alternatively, the imaging transducer 140 may be permanently adhered within the transducer assembly, such as via an adhesive.

Non-limiting examples of the ultrasound imaging transducer include the ultrasound endoscope described in US Patent Publication No. 2015/0209005A1 (Bezanson et al.), titled "Ultrasound Endoscope and Methods of Manufacture Thereof", which is incorporated herein by reference in its entirety, and the ultrasound imaging device disclosed in International PCT Patent Publication No. WO2017127328 A1 (Brown et al.), titled "Compact Ultrasound Device Having Annular Ultrasound Array Peripherally Electrically Connected to Flexible Printed Circuit Board and Method of Assembly Thereof", which is incorporated herein by reference in its entirety. It will be understood that these devices are provided only as illustrative examples, and that a wide variety of ultrasound imaging devices may be integrated within the ultrasound transducer assembly. Furthermore, while the example embodiments included herein describe ultrasound imaging transducers that are disposed co-axially with the axis of the acoustic lens of the therapeutic transducer, it will be understood that the imaging axis need not be co-axial with the axis of the acoustic lens, provided that the focal region of the therapeutic ultrasound lies within an imaging region associated with the imaging transducer.

The configuration shown in FIG. 2 provides one example implementation of the orientation of the ablation lens relative to the endoscope. In one example implementation, the endoscope tip may be recessed from the lens curvature so that the endoscope does not occlude the ablation tool, while still having the ablation zone centered in the imaging window. The lens-composite stack may be encased to ensure the composite remains air-backed. During preliminary testing of an example co-registered device, described in the examples below, it was found that, with the current drive electronics and the missing lens area needed to accommodate the imaging probe, a higher voltage was needed to consistently cavitate relative to the design without a co-registered imaging array.

Figure 3:
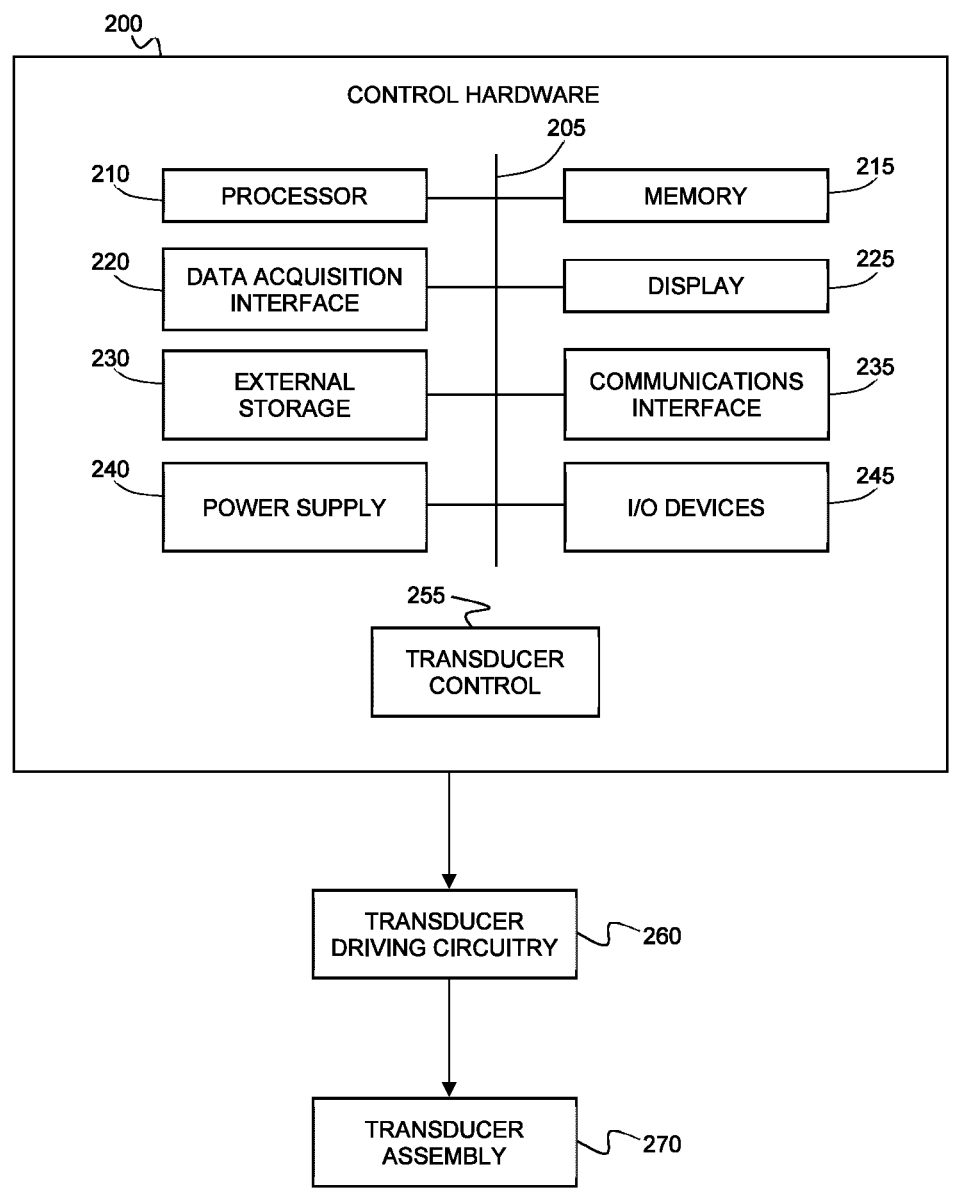
FIG. 3 shows an example system for generating therapeutic focused ultrasound.

FIG. 3 provides a block diagram illustrating an example implementation of a system for performing procedures involving focused ultrasound, such as histotripsy or HIFU. The control hardware 200 is operably connected to the transducer driver electronics/circuitry 260, which drives the transducer assembly 270 to generate focused ultrasound. The driver electronics/circuitry 260 may comprise, for example, a high-voltage single ended ultrasound pulser.

For example, in the case of a histotripsy system, the driver electronics/circuitry 260 may be capable of supplying over 200 volts (e.g. over 400, 600, 800 or 900 V), for example, at up to 144 amps of pulsed current, or 24 amps continuous current.

The control hardware 200 includes one or more processors 210 (for example, a CPU/microprocessor), bus 205, memory 215, which may include random access memory (RAM) and/or read only memory (ROM), a data acquisition interface 220, a display 225, external storage 230, one more communications interfaces 235, a power supply 240, and one or more input/output devices and/or interfaces 245 (e.g. a speaker, a user input device, such as a keyboard, a keypad, a mouse, a position tracked stylus, a position tracked probe, a foot switch, and/or a microphone for capturing speech commands).

The control hardware 200 may be programmed with programs, subroutines, applications or modules, such as transducer control module 255, which include executable instructions, which when executed by the one or more processors 210, causes the system to generate a series of pulses suitable for a selected type of focused ultrasound therapy. Such instructions may be stored, for example, in memory 215 and/or other storage.

The control hardware 200 may be implemented as one or more physical devices that are coupled to processor 210 through one of more communications channels or interfaces. For example, control hardware 200 can be implemented using application specific integrated circuits (ASICs). Alternatively, control hardware 200 can be implemented as a combination of hardware and software, where the software is loaded into the processor from the memory or over a network connection.

Figure 4:
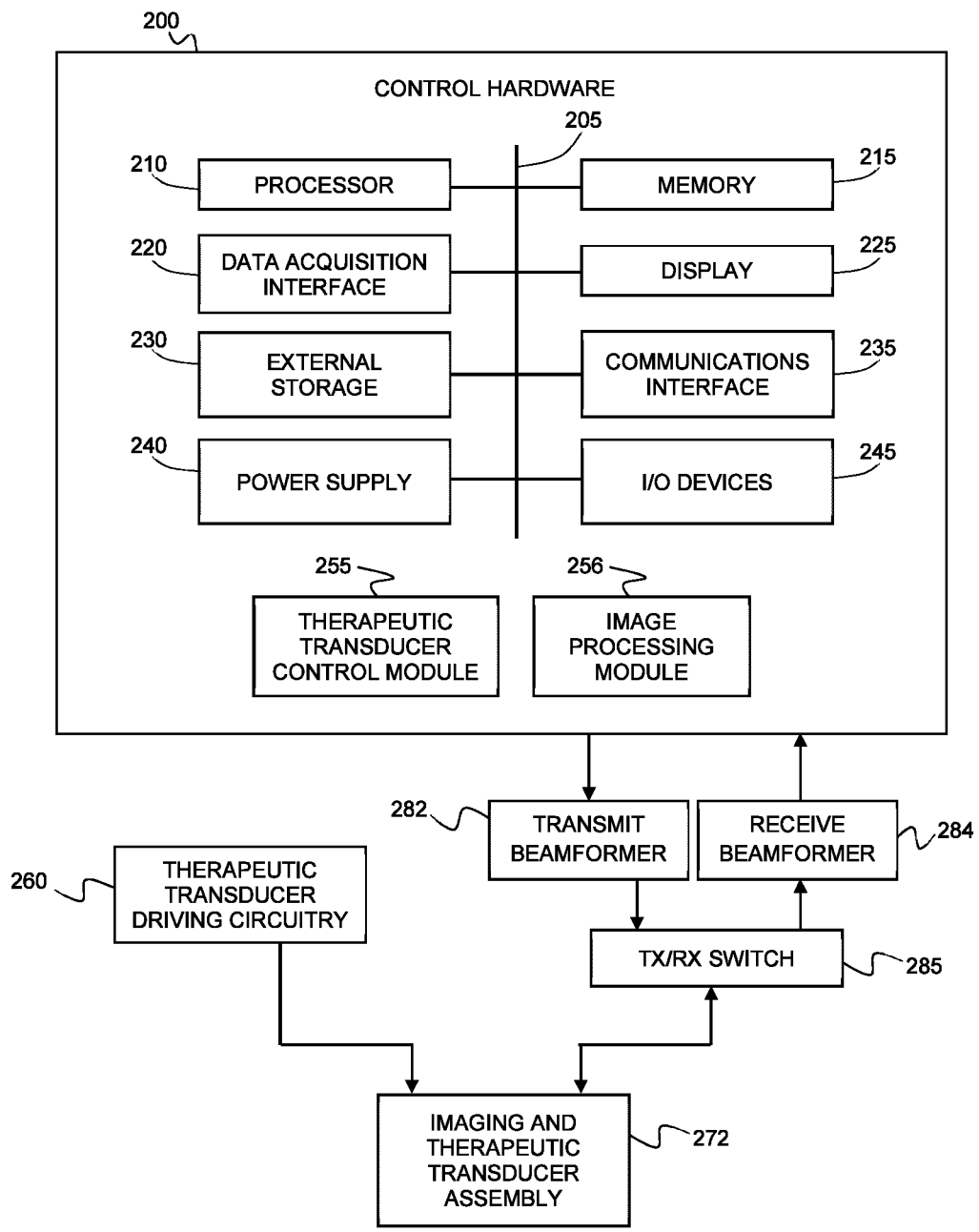
FIG. 4 shows an example system for generating therapeutic focused ultrasound and performing ultrasound imaging.

FIG. 4 illustrates an example embodiment of a system configured for focused ultrasound therapy and imaging using a transducer assembly 272 having an integrated co-registered imaging transducer and a focused ultrasound therapeutic transducer. Control hardware 200 is employed to control transmit beamformer 282 and receive beamformer 284, and Tx/Rx switch 285, and for processing the beamformed receive signals. As shown in FIG. 4, in one embodiment, control hardware 200 may include an image processing module 256 for processing image data obtained using the co-registered imaging transducer.

The example embodiments disclosed above may be employed for a wide variety of applications, such as neurological procedures. Currently, one of the most common methods of tumor resection in the brain is the use of burr-hole surgery, in which a hole is made in the skull and, using visual guidance as well as pre-operative MRI images, a cavitational ultrasonic surgical aspiration (CUSA) device is used to ablate the tumor tissue. This CUSA treatment is a contact ablation where the device cavitates and ablates tissue adjacent to the tip and the liquified tissue is then pulled away via suction. Although effective, the surgeon cannot visualize below the surface and ablate at the same time using this method; therefore, it is proposed that if a histotripsy device could be made which both images and ablates and this device could additionally be made small enough to enter a burr hole, that this device could potentially be used as a replacement to the CUSA tool.

Although many of the example embodiments described herein pertain to histotripsy, it will be understood that the systems and devices disclosed herein may be employed for focused ultrasound applications other than histotripsy. In some example embodiments, the systems and devices disclosed herein can be used for HIFU. In some example implementations, the embodiments disclosed herein could be used for HIFU without the presence of the polymer acoustic impedance matching layer, and/or with a different lens material, and/or using a non-composite piezoelectric layer. Furthermore, the distal lens shape may be spherical in the case of HIFU applications, as HIFU does not typically require the high intensity of ultrasound that histotripsy does, and instead involves the sustained delivery of ultrasound to heat tissue.

EXAMPLES

The following examples are presented to enable those skilled in the art to understand and to practice embodiments of the present disclosure. They should not be considered as a limitation on the scope of the disclosure, but merely as being illustrative and representative thereof.

In the following examples, a small, 10 mm aperture histotripsy transducer was characterized and, following characterization, the device was modified to include a co-linear, co-registered 40 MHz imaging device to allow both imaging and ablation in real-time with a 10 mm aperture. These examples demonstrate the feasibility of a hand-held tool that is sufficiently small to be used in neurosurgery, as well as other endoscopic surgery requiring high-resolution imaging and tightly focused ablation zones.

Example 1: Fabrication of Transducer Assembly

Figure 5:
FIG. 5 is a photograph of an example focused ultrasound assembly including a piezoelectric composite that adhered to and impedance matched to an elliptical aluminum acoustic lens (6061 aluminum), where the lens is coated with a layer of Parylene C.

The ultrasound ablation transducer described in the present example consists of an air-backed piezoelectric composite bound to an aluminum lens using epoxy, where the aluminum lens has a quarter wavelength matching layer on the front face matching to water. A photograph of the assembled composite transducer and coated parabolic aluminum acoustic lens is shown in FIG. 5.

The piezoelectric composite was designed to provide maximum output power near 5 MHz with the composite itself being a 1-3 PZT-polymer dice-and-fill design. The composite was modeled using in-house Krimholtz-Leedom-Matthaei (KLM) code, which provided a design thickness of 303 µm and a pillar geometry resulting in a characteristic acoustic impedance of approximately 17 MRayls, closely matching the characteristic impedance of 6061-T6 series aluminum. The composite was attached to the aluminum lens using a thin film of Epotek 301 epoxy resin (Epoxy Technology Inc.), which is known to have an acoustic impedance of 3.05 MRayls (at 30 MHz). It is noted that this acoustic impedance is lower than the acoustic impedances of both the acoustic lens and the piezoelectric layer.

The aluminum lens was fabricated using a CNC milling process and designed to focus at a 7 mm depth. The curvature of the lens was fabricated to be elliptical, as per the equation provided above. As noted above, elliptical lens shape avoids spherical aberrations in the lens, which are important to avoid when the lens focus is smaller than the lens aperture.

A quarter-wavelength Parylene matching layer was deposited on the lens face using the Specialty Coating Systems PDS-2010 Parylene Coater (Specialty Coating Systems Inc., Indiana USA). Parylene has a longitudinal speed of sound of 2135 m/s with an acoustic impedance of 2.75 MRayls [20], so a layer thickness of 78.2 µm was deposited to match at 6.82 MHz.

As noted above, the epoxy film thickness and properties could be chosen to modify the transducer output, where, for example, increasing film thickness attains improved acoustic power output for a given input voltage but with a reduced efficiency and bandwidth, as well as a frequency shift of the resonance. For the present device, KLM models (described below) show the film thickness is near 20 µm, approximately doubling output power compared to having no film for a fixed drive-voltage while also shifting the maximum output frequency from 5 MHz to 6.8 MHz. This doubling of output power should result in a sqrt(2) gain in acoustic pressure at the lens focus.

Example 2: Experimental and Simulation Results for Transducer Assembly without Integrated Ultrasound Imaging Transducer Characterization of the transducer was performed by the following methods: electrical impedance measurements both before and after lens bonding, measuring a pressure field map near the transducer focus, obtaining a measure of the peak minimum focal pressure versus drive voltage, and imaging of a single-cycle pulse generated bubble cloud. The experimental electrical impedance, measured using an Agilent 4294A Precision Impedance Analyzer (Agilent Technologies, Santa Clara, USA), and the KLM derived electrical impedance are shown in FIGS. 6A and 6B for a 10 mm diameter disc of air backed and air loaded composite prior to attaching a lens.

As described above, in-house created KLM code was used to model the transducer electrical impedance. This code was able to model not only a bare piezoelectric composite, but the full transducer stack which included an epoxy bonding layer and aluminum lens. To include the lens in the KLM model, the composite-lens stack was divided into a set of concentric rings of equal area, each with equal backing, composite, epoxy and Parylene layers, but with aluminum layer of varying height to account for the lens curvature varying as a function of radius. For example, at the center of the lens, a ring would be modeled as having a 2 mm aluminum layer as part of the lens, while a ring at the outer edge would be modeled with a 4.4 mm aluminum layer as the lens curvature is larger at the outer edge. Once each ring was modelled in KLM separately, the electrical impedances for each ring were combined in parallel to reconstruct the true device impedance.

For the KLM model to match impedance measurements, measured properties, such as composite thickness, volume fraction, density, and effective electro-mechanical coupling factor, were entered into the model while damping coefficient, clamped capacitance, and acoustic impedance were adjustable parameters. By matching KLM with the measured electrical impedance, it was determined that the composite acoustic impedance was 13.8 MRayls, not the 17 design target of MRayls. This suggests increasing the volume fraction of future composite designs is needed. However, for this 13.8 MRayl composite, the transmitted power to the lens is calculated to be 98.9% based on the acoustic impedance mismatch and, as the purpose for matching composite to lens was to maximize power transfer, a 1.1% loss is acceptable.

FIGS. 7A and 7B show the measured impedance and phase curves, respectively, for a transducer with the lens attached. As can be seen in FIG. 7A, the resonance peak normally seen for a composite is absent, as the lens spreads the resonances out over a wide band. Referring again to FIGS. 6A and 6B, it is of note that near 8 MHz in the measured impedance is a second resonance feature corresponding to a lateral mode of the composite which is not captured in KLM, as KLM is inherently a one-dimensional model. This one-dimensional limitation also leads to difficulties in modeling the full transducer electrical impedance when a lens is introduced.

This difficulty is demonstrated in FIGS. 7C and 7D, where a comparison is shown between the measured electrical impedance for a composite with lens attached, along with KLM models both with and without Epotek 301 between the composite and lens. The measured impedance magnitude in FIG. 7C shows a resonance at 5 MHz and an anti-resonance at 7 MHz; however, a KLM model with composite in direct contact to the lens shows only a decreasing impedance magnitude with increasing frequency. The addition of a 20 µm epoxy layer is therefore necessary to capture the measured system behavior in the model. Also of note are a number of small, 5 Ohm amplitude oscillatory features between 2 MHz and 7 MHz that are visible in the measured impedance. These variations are likely caused by internal reflections from the face and sides of the lens back to the composite. A smaller version of the variation is captured by the KLM models which can be seen in the KLM model plots. The difference in magnitude of these smaller resonances is likely caused by the model assuming reflections are 1-dimensional only and, therefore, cannot travel laterally between the concentric rings in the sectioned KLM model, whereas in the real system these reflections would be normal to the lens surface and travel in many directions within the lens.

The impedance phase curve in FIG. 7D also shows the importance of an epoxy layer where the 20 µm epoxy layer moves the maximum phase point from 4 MHz to 6.5 MHz and increasing the value from −60 degrees to −20 degrees, again, more closely matching to the measured electrical impedance.

When employing further simulations to investigate the effect of epoxy thickness of device output parameters, it was found that the acoustic power transfer of a transducer having an acoustic lens bonded to a piezoelectric material via an epoxy layer was dependent on the epoxy thickness. For example, simulations demonstrated that as the thickness of the epoxy layer is increased, the power transfer of device increases, albeit with reduced efficiency and bandwidth, as well as a frequency shift of the resonance. The effect of variations of epoxy thickness on device properties are illustrated in FIGS. 8-10 below.

In FIGS. 8A and 8B, the simulated electrical impedance of five transducer designs is shown, with each device having an increasing epoxy layer thickness. For the magnitude plot shown in FIG. 8A, the resonance (minimum point) grows deeper, and the anti-resonance (peak) grows higher, as the frequency of both shifts lower. In the phase plot shown in FIG. 8B, the phase peak increases while the frequency also shifts to the left. Without intending to be limited by theory, it is suspected by the inventors that the shift in frequency may be, for example, mass-spring related, or may be a resonance cavity created by the addition of the epoxy.

Figure 9:
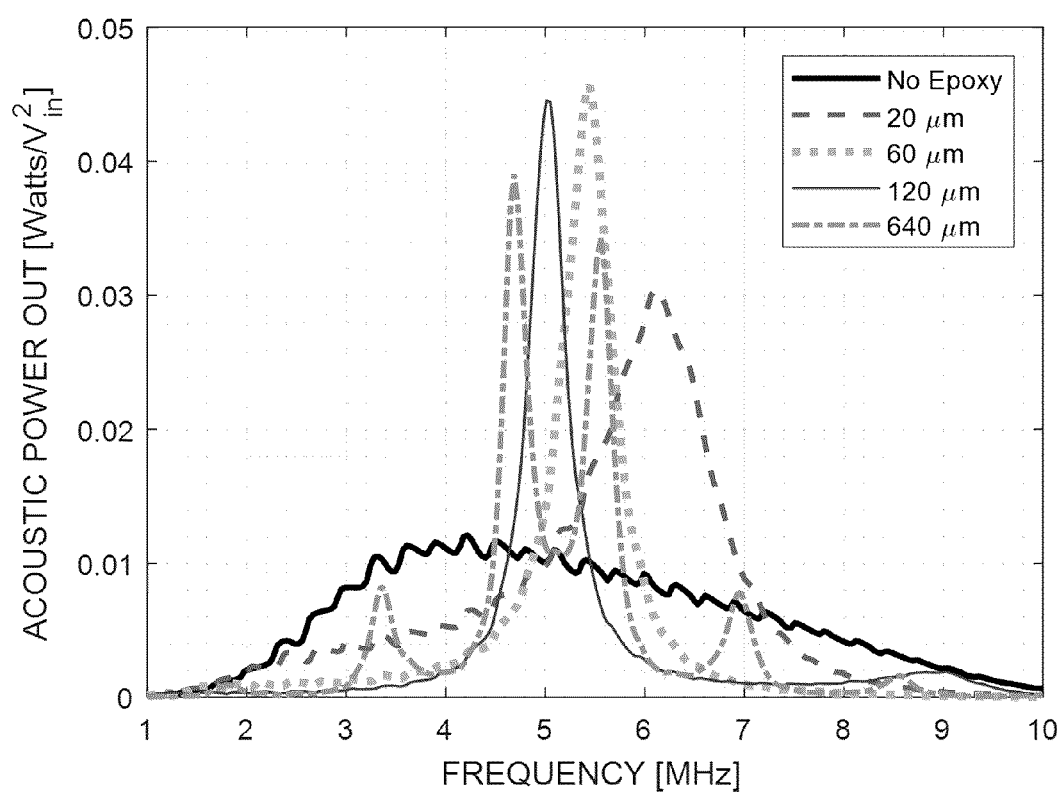
FIG. 9 plots the power spectrum output for each epoxy layer thickness, showing the power output doubling from the case of a device without epoxy to a device having a 120 μm layer of epoxy. As can be seen in the figure, the bandwidth is reduced as the epoxy thickness is increased, as indicated by the much narrower peak for the 120 μm epoxy layer compared to the broadness of the "no epoxy" line.

FIG. 9 plots of the simulated acoustic power output normalized to input voltage squared show a power increase with increasing epoxy layer thickness, up to a limit. In this figure, a quarter wavelength matching layer is added to the front transducer face with a thickness corresponding to wavelength associated with the maximum transducer output power prior to the quarter wavelength layer being added; or, in other words, the quarter wavelength layer is matched to work in tandem with the specific epoxy layer thickness. As can be seen in the figure, the simulated devices having layer thickness of 60 micrometers and 120 micrometers of provide an almost identical power output, with a shifted frequency between them, while increasing further to a 640 micrometer layer creates a split output with reduced power in each band, compared to the devices with 60 and 120 micrometer layers. It is also noted that according to the model, power output is increased by a factor of up to 3.75 by adding the epoxy layer.

Figure 10:
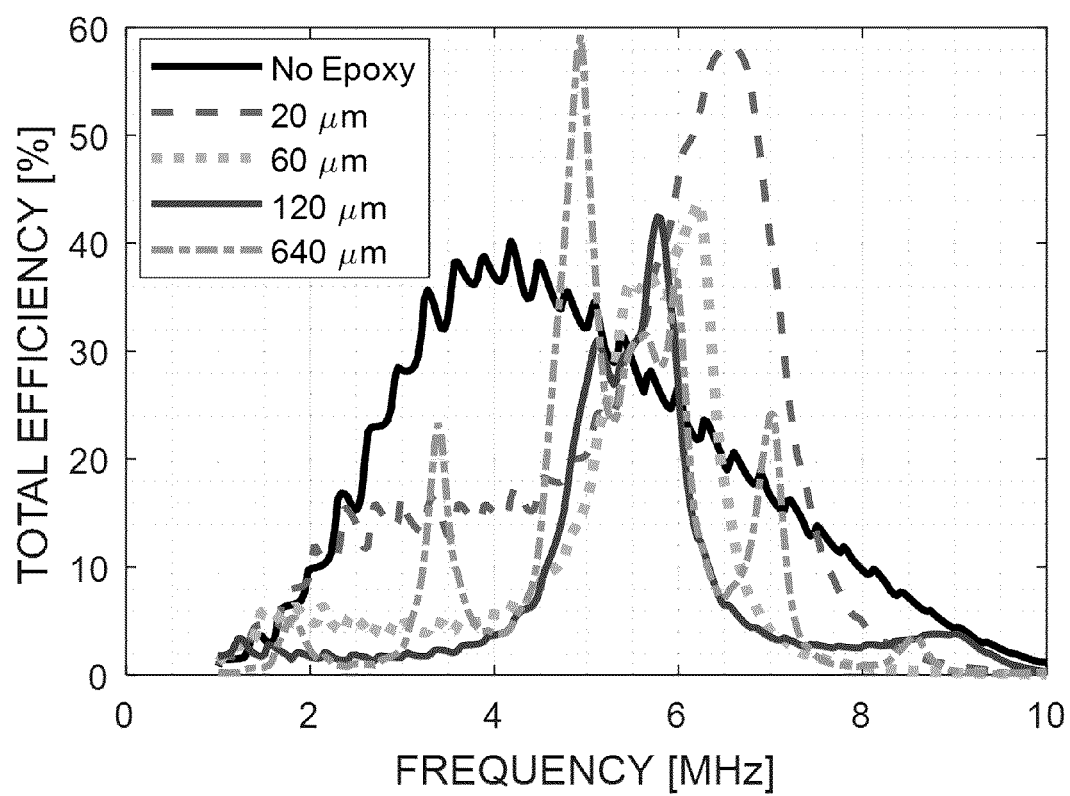
FIG. 10 plots simulated transducer efficiency for a device without epoxy as well as devices with 20, 60, 120, and 160 micrometers of epoxy, as a function of drive frequency. The addition of epoxy increases efficiency, but narrows the band in which the system is more efficient.

FIG. 10 illustrates how simulated efficiency changes as the bonding epoxy layer is widened, where it is observed that the epoxy layer increases efficiency, albeit over a narrower band of frequencies.

Figure 11A:
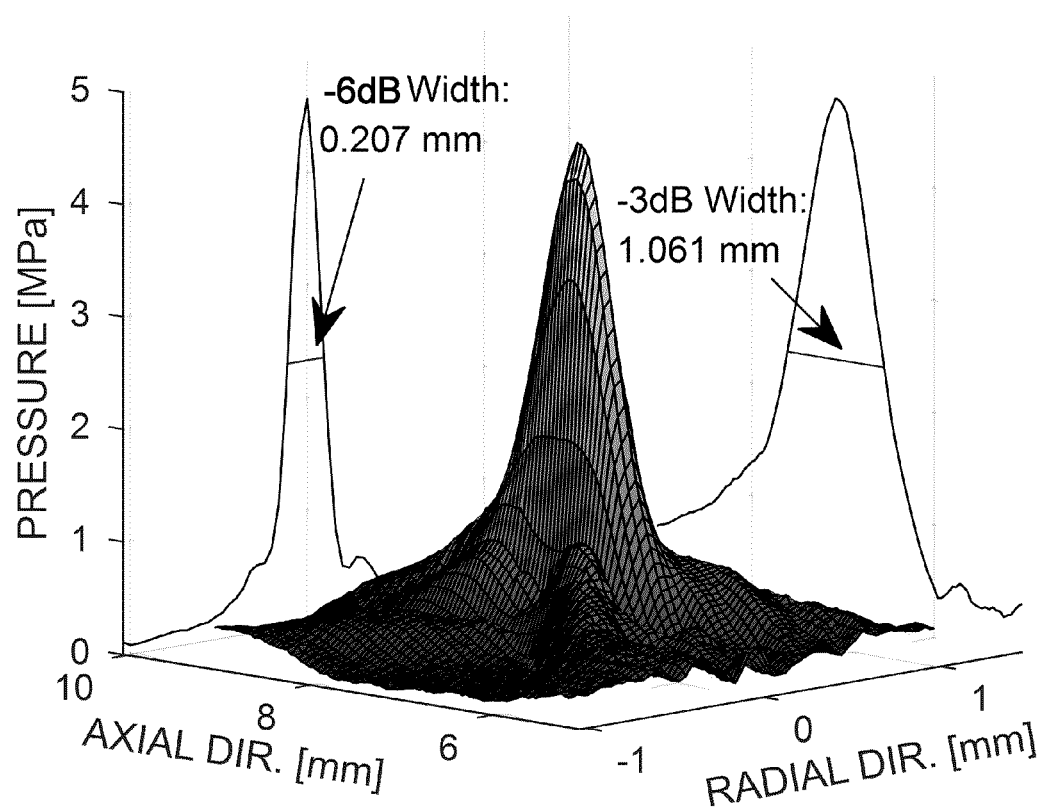
FIGS. 11A and 11B plot the measured pressure profile for the transducer assembly without an integrated co-registered imaging transducer, when the therapeutic transducer is driven at a drive voltage of 20 V, a frequency of 6.8 MHz, and 20 cycles in the burst signal.

With an impedance model of the transducer built and verified, a measure of the pressure field near the focus was performed using a 0.04 mm needle hydrophone (Precision Acoustics Ltd., Dorchester, UK) with a 7 MHz sensitivity of 5 nV/Pa. This pressure field is shown in FIG. 11A, which plots the 2D pressure profile where the −6 dB radial beam width is 0.207 mm, and the −6 dB axial beam length is 1.061 mm. The pressure field was measured in a 5 mm×2 mm plane intersecting the transducer focus where the plane normal vector is perpendicular to the direction of acoustic propagation. Using an XYZ-stage capable of micron accuracy and repeatability, the 0.04 mm needle hydrophone was scanned through the pressure field, where an oscilloscope recorded the peak-negative pressure while the transducer was driven using a pulser based on the design by Brown and Lockwood [21] with a 20 cycle, 20 V, 6.8 MHz pulse.

Figure 11B:
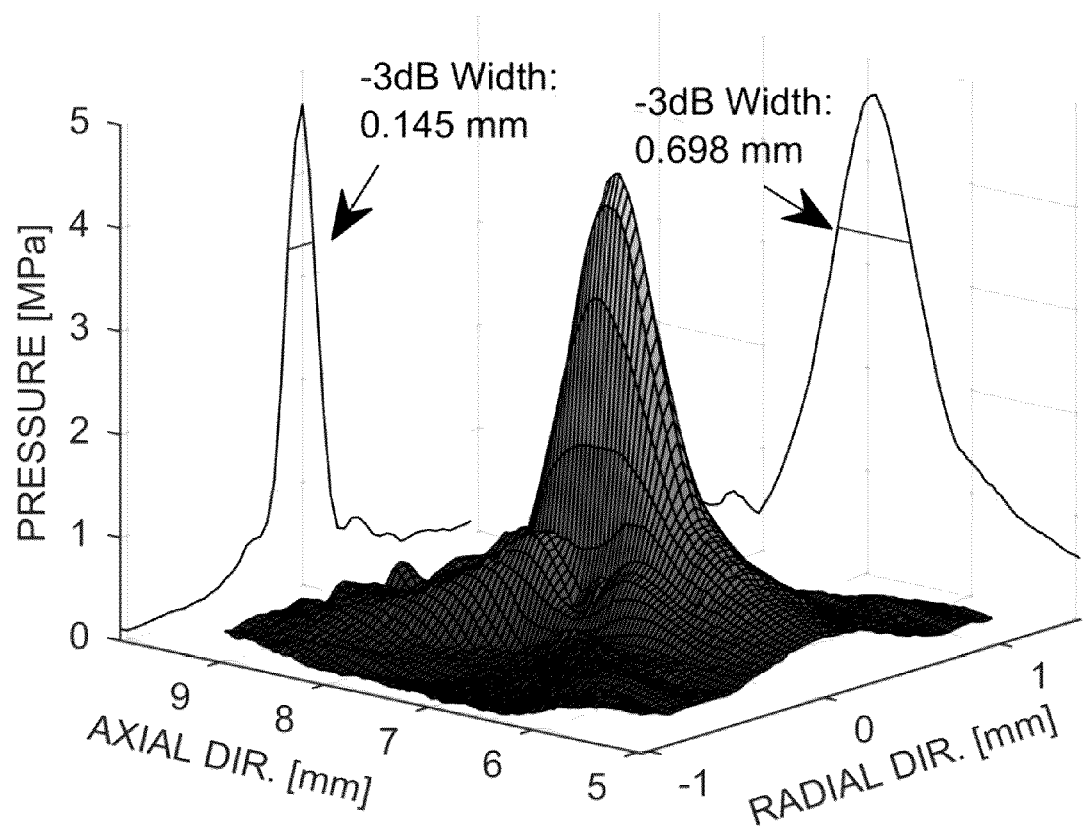

FIG. 11B shows that the −3 dB width in the radial direction is 0.145 mm while in the axial direction the −3 dB width measures 0.698 mm. An important aspect of performing this measurement is ensuring there is a single, sharp focus for this transducer so that no secondary lobes could also cause ablation in tissue.

With the pressure field mapped, focal pressure as a function of drive voltage was measured to confirm the possibility of reaching the intrinsic cavitation threshold needed for histotripsy (26.1-27.9 MPa at 3 MHz in water [E. Vlaisavljevich, K.-W. Lin, A. Maxwell, M. T. Warnez, L. Mancia, R. Singh, A. J. Putnam, B. Fowlkes, E. Johnsen, C. Cain, and Z. Xu, "Effects of ultrasound frequency and tissue stiffness on the histotripsy intrinsic threshold for cavitation," Ultrasound in Medicine and Biology, vol. 41, no. 6, pp. 1651-1667, 2015]). The transducer focal pressure was measured using a hydrophone as a function of drive voltage.

Figure 12A:
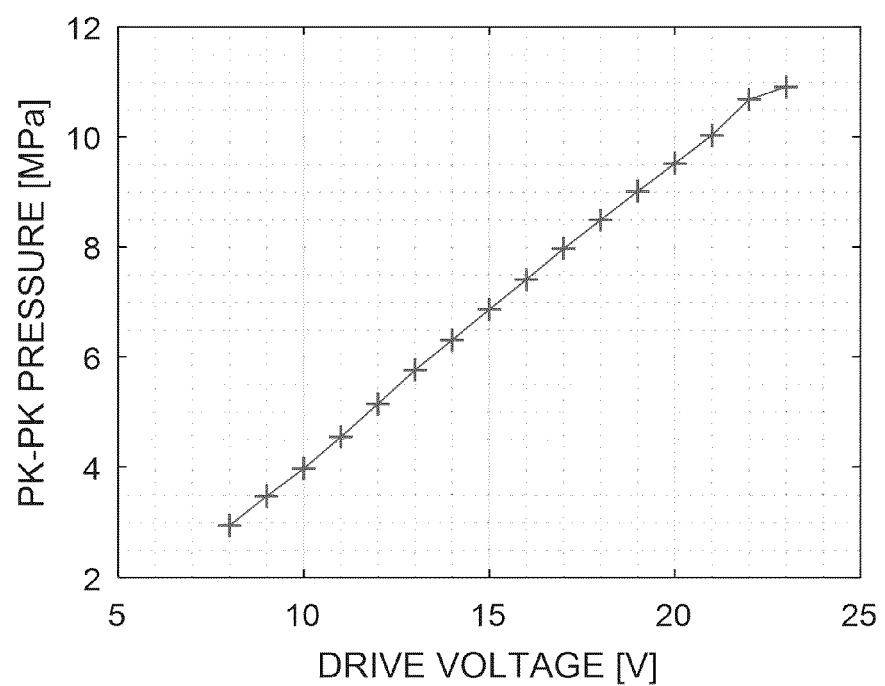
FIGS. 12A and 12B plot the peak-to-peak pressure vs. drive voltage for the non-imaging transducer.
Figure 12B:
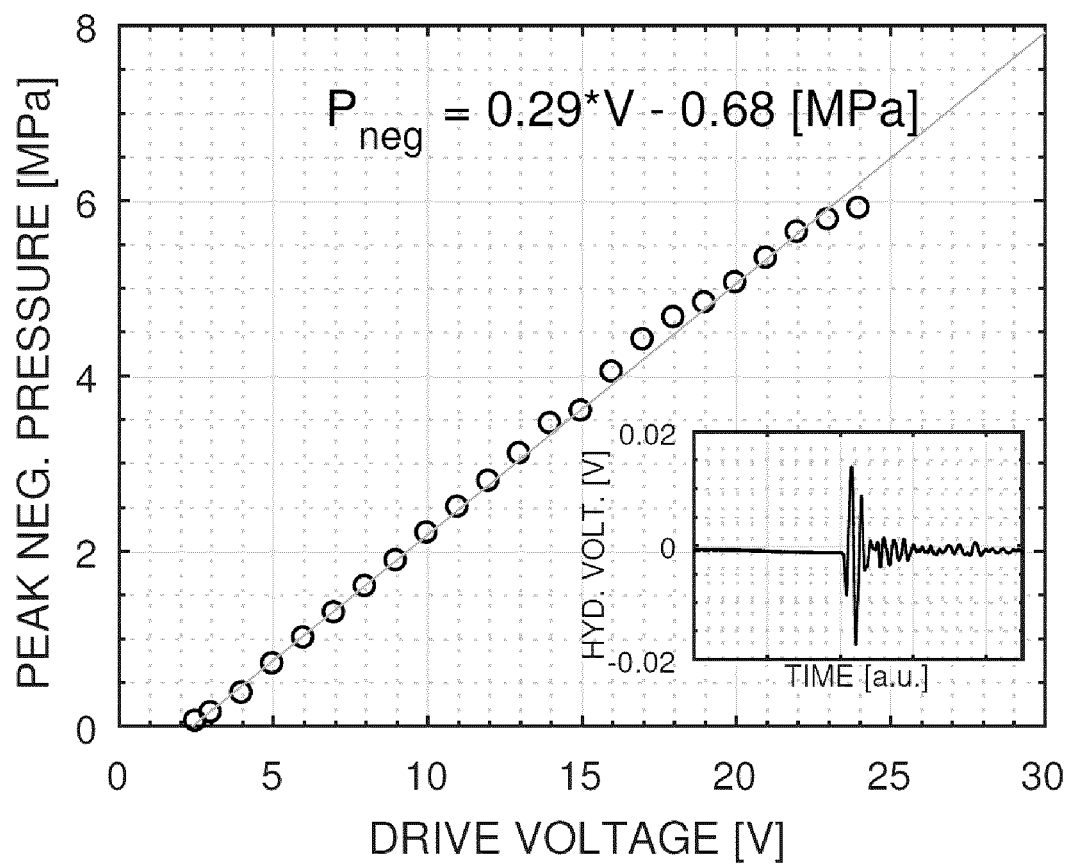

In FIG. 12A, the peak-to-peak pressure versus drive voltage for the non-imaging transducer is shown. The measurement was limited to below 25 V as, above this, large oscillations in the hydrophone measurements were observed, which were believed to be the beginnings of cavitation, which could potentially damage the hydrophone. FIG. 12B shows an alternative representation of the data plotted in FIG. 12A, plotting the peak-negative pressure (the maximum negative value of pressure instead of the difference between the maximum and minimum pressure). The inset to FIG. 12B plots a representative one-way single-cycle pulse response as measured at the hydrophone to provide device bandwidth. Within the inset, temporal ringing following the main pulse is likely a result of reverberation within the lens, and potentially also ringing within the hydrophone which could not be uncoupled from the measurement.

A linear relationship between pressure and drive voltage is seen from 2.5 V up to 17 V. Above 17 V, initial evidence of cavitation at the hydrophone tip was seen as noise in the oscilloscope signal. At 25 V, cavitation at the hydrophone tip made pressure measurements inconsistent and, therefore, measurements were stopped. The inset plot shows a one-way, single-cycle pulse response as measured with the hydrophone. The ringing after the initial pulse is due to reverberations within the lens. The pulse bandwidth was 59%.

The transducer was driven with a 20-cycle pulse train to ensure steady-state was reached at 6.8 MHz with a pulse repetition frequency of 100 Hz. A minimum drive voltage of 2.3 V was needed for the drive circuit to power the transducer, after which point the pressure follows a linear trend of 0.29 MPa/V up to 25 V. Following a linear extrapolation, to reach the water intrinsic threshold a drive voltage of greater than 90 V should be needed for a multi-cycle pulse.

Since using a long pulse train is known to increase the length of the focal zone, after characterizing the steady-state behaviour, initial experiments with cavitation were then performed using single-cycle pulses in an attempt to create the smallest, most precise bubble cloud possible. A representative single-cycle pulse, as measured at the hydrophone, is shown inset into FIG. 12B, where the pulse has a fractional bandwidth of 59%. In initial single-cycle pulse experiments, a cavitation bubble cloud in water wasn't observed until reaching a minimum drive voltage of 173 V, which is due a single-cycle pulse not reaching the same peak amplitude as the 20 cycle pulse train used to create the data set shown in FIG. 12B. It should be noted, however, that a single-cycle pulse will create a smaller cloud, allowing for more precise tissue ablation.

Figure 13A:
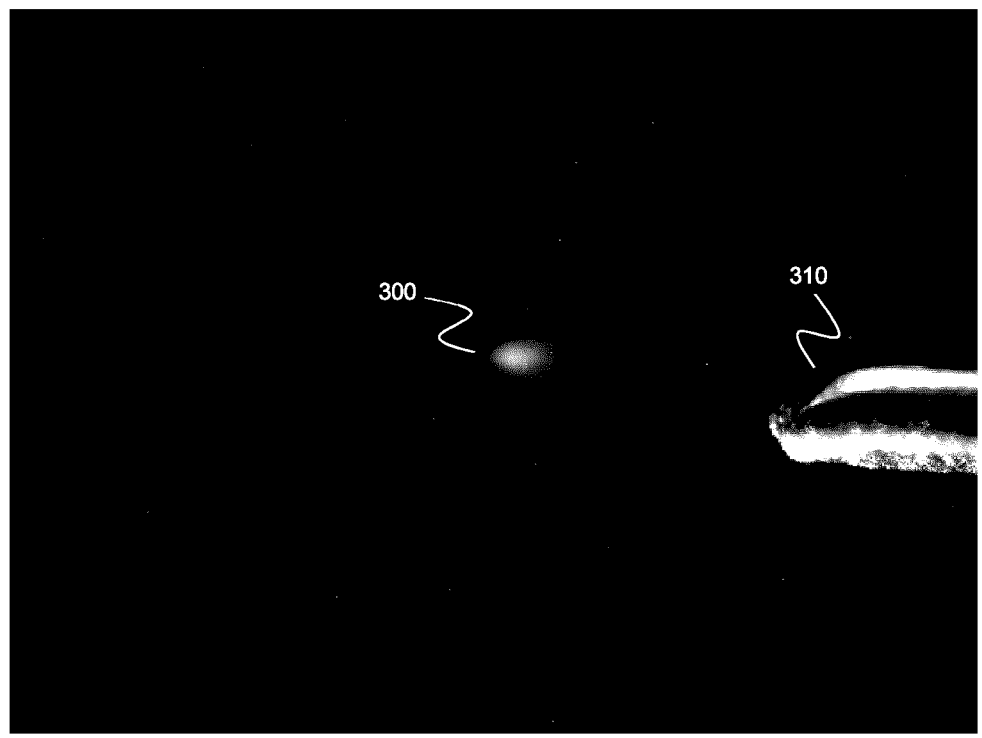
FIGS. 13A and 13B are photographs showing a bubble cloud. The photograph shown in FIG. 10A was generated with a 170V, 3 cycle pulse with a 10 ms repetition rate. The photograph shown in FIG. 10B was generated in degassed, deionized water with a 6.8 MHz single-cycle, single-ended 173 V pulse at a 50 Hz repetition rate. The needle tip shown the right is a 26 gauge needle with a diameter of 0.46 mm, demonstrating that the cloud size measures ~0.2 mm diameter vertically at its smallest size.

It was found for this device, at least 170 V was required to create any bubble. The bubble cloud was identified visibly using a microscope, where it can be seen in FIG. 13A at 300. The bubble cloud was generated with a 170V, 3 cycle pulse with a 10 ms repetition rate. The needle tip shown the right (at 310) is a 26 gauge needle with a diameter of 0.46 mm, demonstrating that the cloud size measures ~0.2 mm diameter vertically at its smallest size. The bubble cloud appears blurry because a time average of frames was used while illuminating the bubble cloud to get the image. The cloud measures ~200 um diameter at the narrowest point and ~300 um along the longest axis. The bubble cloud size increases and cavitation action becomes more aggressive as drive voltage and number of burst cycles increases. This can be used to control the speed and amount of tissue being ablated at a time.

Figure 13B:
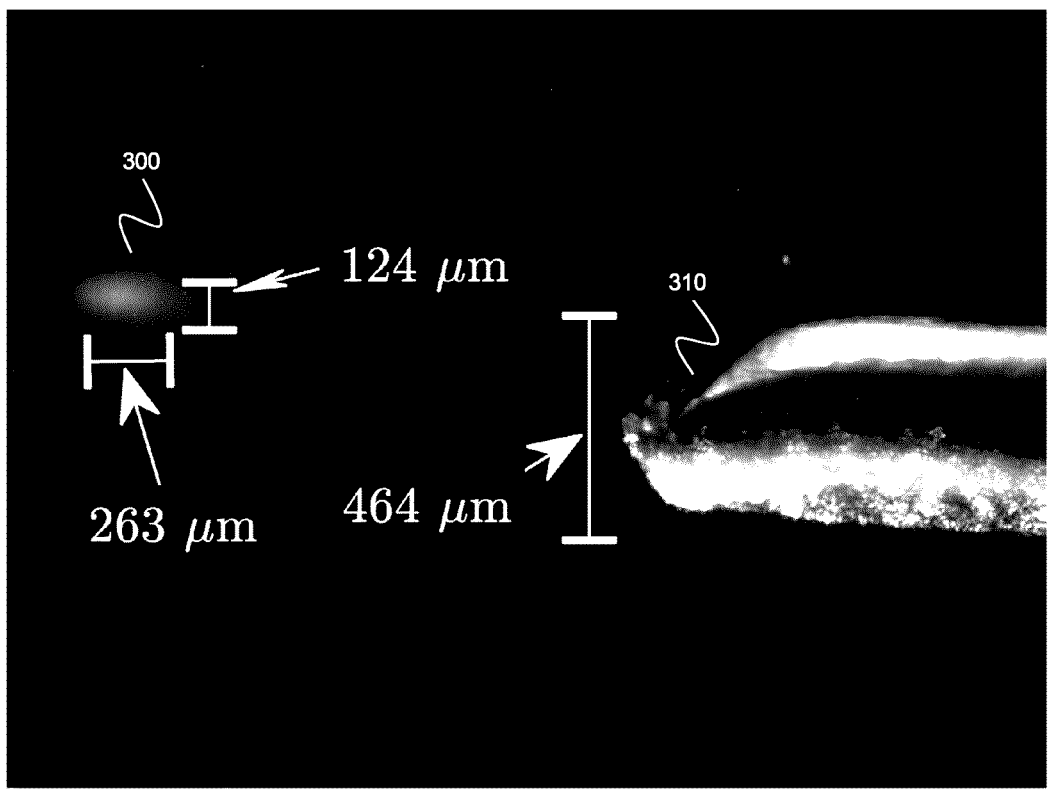

Results from subsequent measurements are shown in FIG. 13B. The cavitation bubble cloud is shown as a white spot here due to averaging of multiple camera frames to produce an image. This bubble cloud was generated in degassed, deionized water with a 6.8 MHz single-cycle, single-ended 173 V pulse at a 50 Hz repetition rate. A 26 gauge needle, nominal diameter 464 µm, can be seen in the image to provide scale for the bubble cloud which measures 124 µm diameter with a length of 263 µm.

Both images (FIGS. 13A and 13B) demonstrate the ability to create a bubble cloud, however, FIG. 13B involved a longer time between pulses, and was only a single-cycle pulse. The smaller size of the bubble in FIG. 13B can be attributed to the lower number of cycles as this makes the overall volume which exceeds cavitation pressure smaller.

Imaging was performed using a Zeiss Discovery.V20 Stereo Microscope and a Zeiss Axiocam ERc 5s digital camera (Carl Zeiss Microscopy GmbH, Jena, Germany) where the bubble cloud was illuminated perpendicular to the direction of imaging, and multiple images were acquired and averaged to recreate the full bubble cloud shape. This imaging is easy to do while cavitation occurs in water; however, in tissue, visual imaging would be impossible at-depth, so the tool presented here can instead be modified with the addition of a central hole, allowing an ultrasound probe through the center to image while ablation is being performed.

Example 3: Experimental and Simulation Results for Transducer Assembly with Integrated Ultrasound Imaging Transducer In the present example, a co-registered imaging and ablation tool is described. In order to create a co-registered imaging and ablation device, the focusing lens, which was schematically illustrated in FIG. 1, was modified to add a 4 mm×4 mm hole through the center allowing any imaging tool to image the ablation area, as illustrated in FIG. 2. The imaging device employed in the present example was developed in-house, and was fabricated as a 40 MHz, 64-element phased-array transducer packaged in a 2.5×3.1 mm endoscopic form factor. This endoscopic phased array was fully characterized by Bezanson et. al. in 2014 [A. Bezanson, R. Adamson, and J. A. Brown, "Fabrication and performance of a miniaturized 64-element high-frequency endoscopic phased array," IEEE Transactions on Ultrasonics, Ferroelectrics, and Frequency Control, vol. 61, pp. 33-43, January 2014.], and US Patent Publication No. 2015/0209005A1. The imaging beamformer used was a sub-nyquist, variable sampling, high-frequency phased array beamformer presented by Samson et. al. in 2017 [C. A. Samson, A. Bezanson, and J. A. Brown, "A sub-nyquist variable sampling, high-frequency phased array beamformer," IEEE Transactions on Ultrasonics, Ferroelectrics, and Frequency Control, vol. 64, no. 3, pp. 568-576, March 2017.], and in International Patent Publication No. WO2016115638, which is incorporated herein by reference in its entirety.

Figure 14:
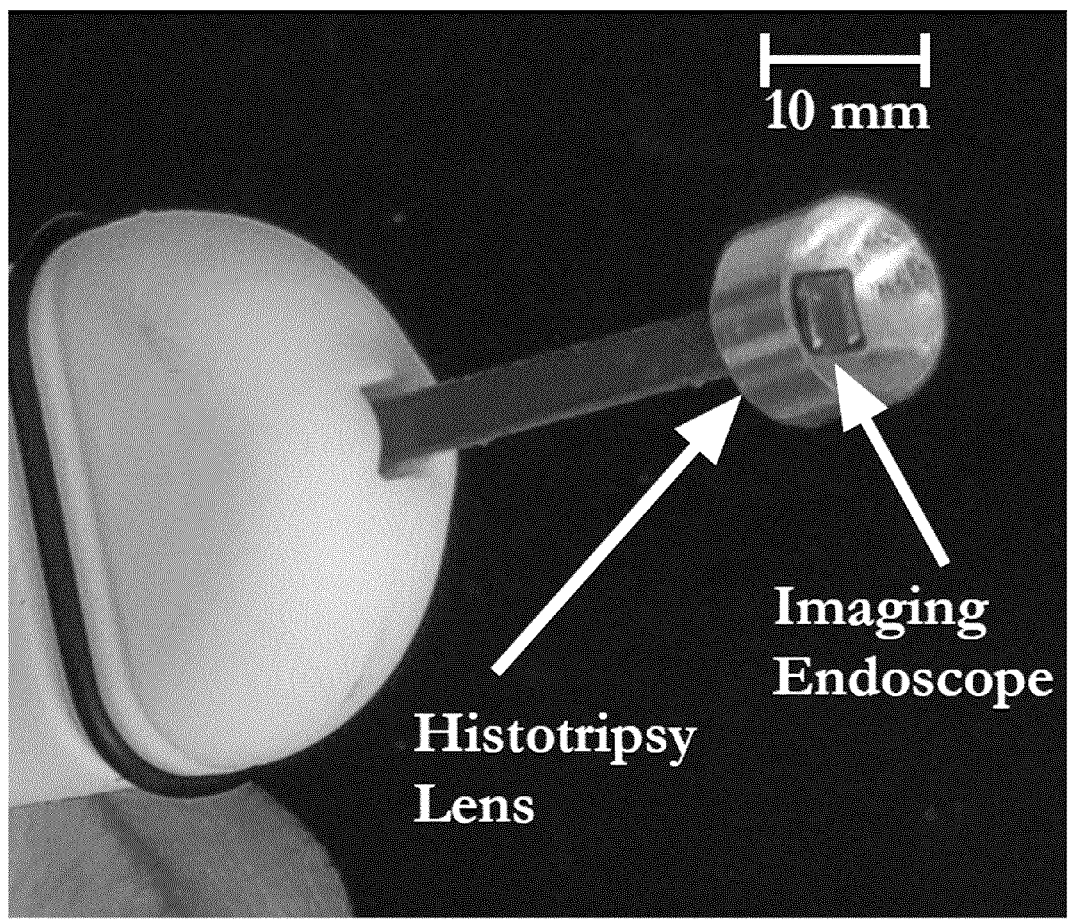
FIG. 14 is a photograph of an example imaging and ablation device, where the histotripsy ablation lens has a center-hole to allow an imaging tool to visualize the area in real-time during ablation. This example imaging device employs a 64-element, 40 MHz phased array endoscope.

FIG. 14 shows the example ultrasound endoscope with a machined lens positioned at the end as was used during co-registered ablation. For surgical applications, the device may be mounted at the end of a hand-held tool for fast user guidance so that ablation points can be targeted on-the-fly if desired. Additionally, the tight lens focus and small ablation spot-size, as well as the high-resolution endoscope imaging window, renders the device as having potential for use in small animal studies where internal ablation, or highly targeted neural ablation with minimal tissue heating, may be desired.

The configuration shown in FIG. 14 provides one example orientation of the ablation lens relative to the endoscope. In one example implementation, the endoscope tip may be recessed from the lens curvature so that the endoscope does not occlude the ablation tool, while still having the ablation zone centered in the imaging window. The lens-composite stack may be encased to ensure the composite remains air-backed. Preliminary testing of the co-registered device found that, with the current drive electronics and the missing lens area needed to accommodate the imaging probe, a higher voltage was needed to consistently cavitate. FIG. 14 demonstrates this need for a higher drive voltage with a plot of pressure vs drive voltage for the transducer with a hole in the center.

Figure 15A:
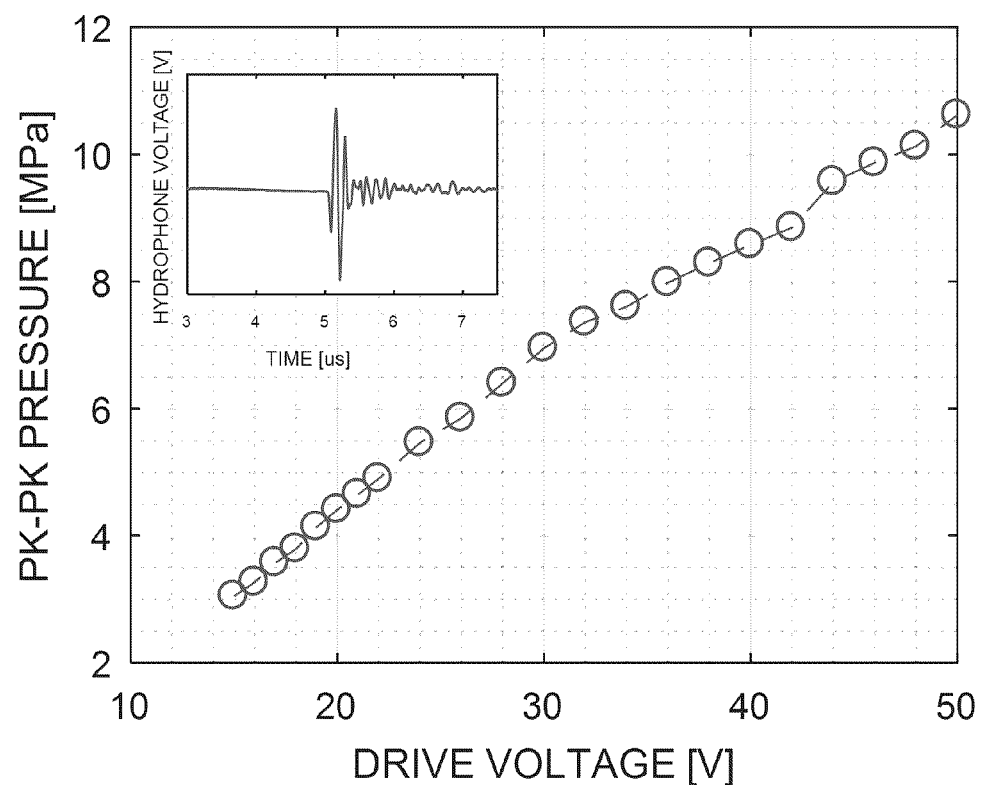
FIGS. 15A and 15B plot the peak-to-peak pressure vs. drive voltage for a transducer assembly having an integrated and co-registered imaging transducer. A one-way single-cycle pulse response is also shown in the top-left corner of FIG. 12A.
Figure 15B:
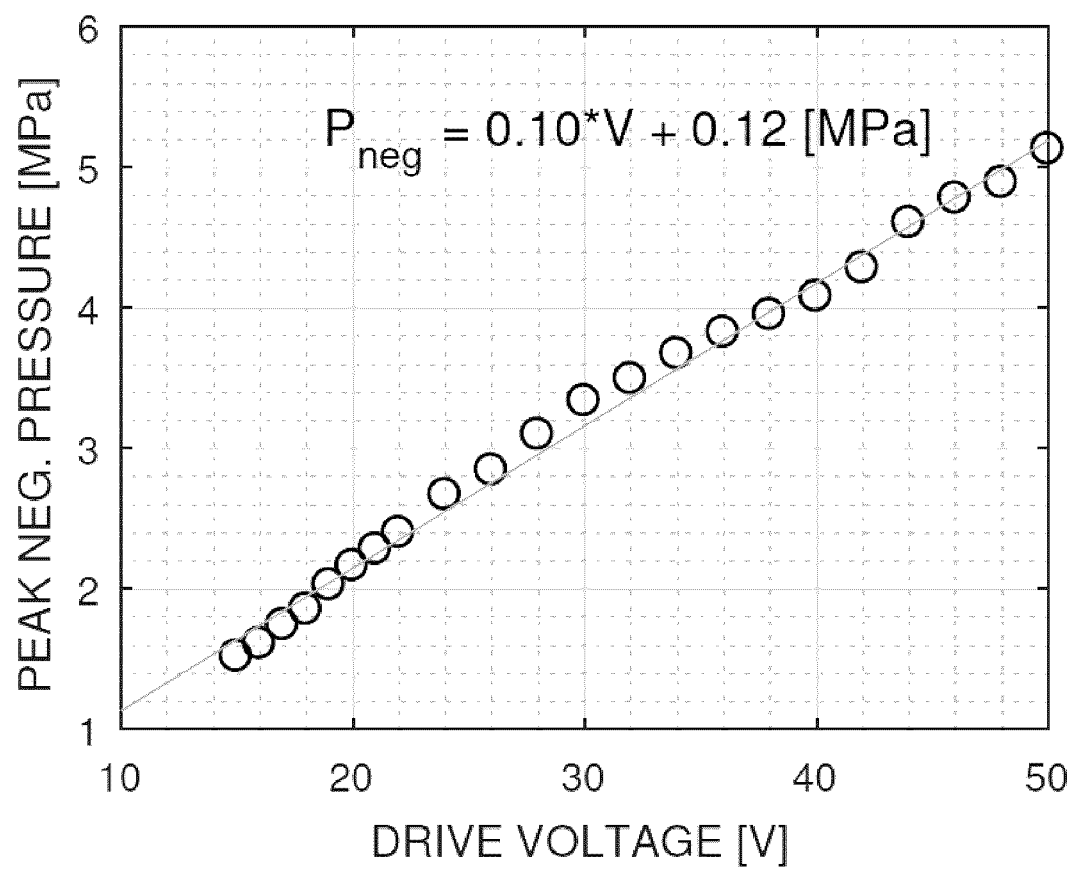

FIGS. 15A and 15B show the peak-to-peak pressure, and the peak negative pressure, respectively, versus drive voltage for the transducer with a hole for co-registration for two different measurements. It is noted that the voltage needed to reach 10 MPa was ~2.5 times larger than for the non-co-registered transducer. This is related to the transducer hole reducing the ability of the transducer to focus. A one-way response to a single cycle pulse at 6.8 MHz is shown in the top-left corner of FIG. 15A, where the response is good, however a tail in the response is seen.

Figure 16A:
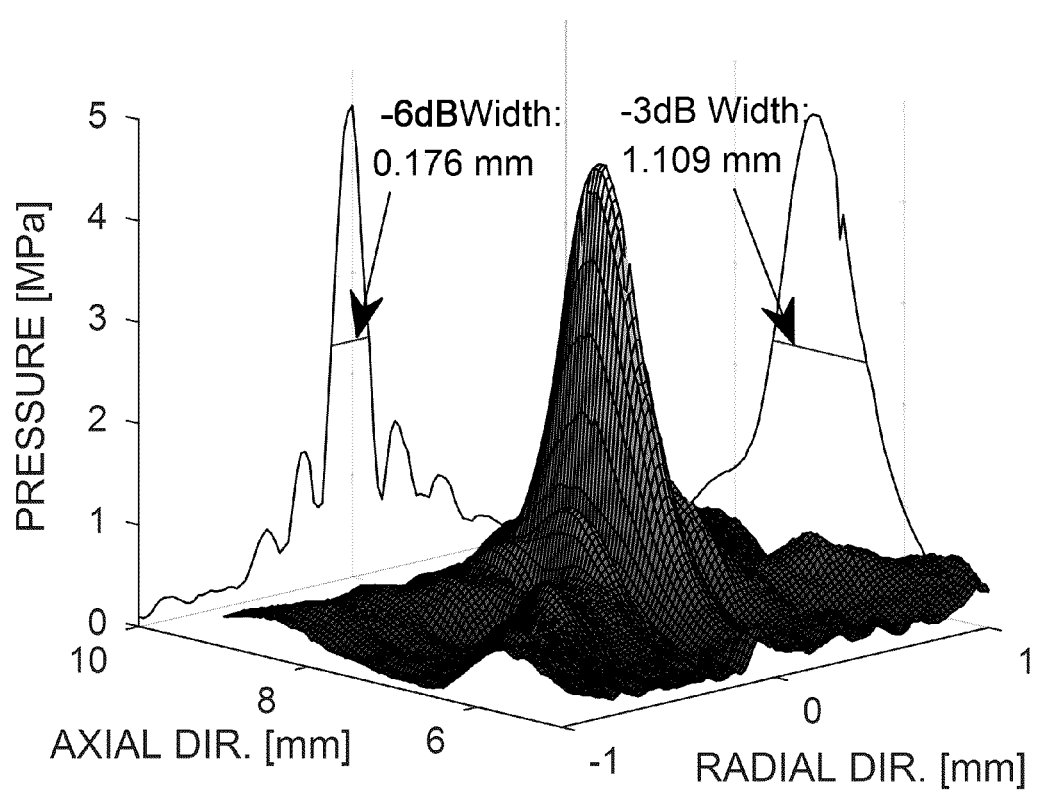
FIGS. 16A and 16B plot the measured pressure profile for the transducer assembly with an integrated co-registered imaging transducer, when the therapeutic transducer is driven at a drive voltage of 40 V, a frequency of 6.8 MHz, and 20 cycles in the burst signal.
Figure 16B:
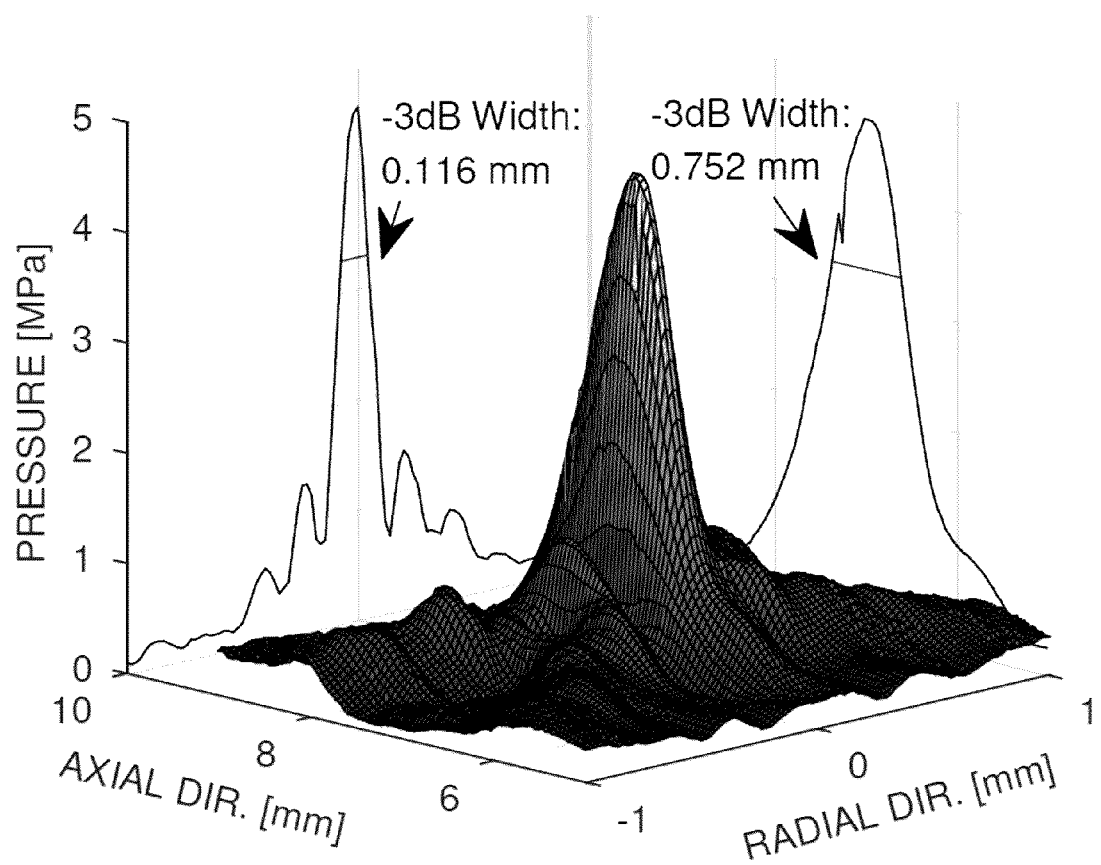

In FIGS. 16A and 16B, the 2D pressure profile of the co-registered transducer is shown, with the −6 dB width shown in FIG. 16A, and the −3 dB width shown in FIG. 16B. The radial beam width appears to be narrower compared to the transducer without a hole, however, there is more energy in the side lobes as seen by the higher pressures off center which is caused by the transducer hole reducing the ability of the lens to focus to a single point. In the measurement shown in FIG. 16B, the pressure field shows visible side lobes at ±0.2 mm, 10 dB below the peak in the radial direction.

In a manner similar to previous measurements made for the non-imaging device, the transducer was driven with a 20 cycle pulse train at 6.8 MHz using a pulse-repetition frequency of 50 Hz. For the non-imaging transducer characterized above, pressure increased at a rate of 0.29 MPa/volt whereas for this co-registered imaging device the pressure increases at a rate of 0.1 MPa/volt. In practice, this made it difficult to cavitate in water for the co-registered device as the pressure is reduced by a factor of 2.9; however, since the shock scattering cavitation threshold in fatty tissue (13.26 MPa at 1000 HZ pulse-repetition frequency) is lower than the intrinsic threshold in water, this device is a good candidate for targeted neural ablation since it can reach the shock scattering threshold for fatty tissue and the brain consists of a high percentage of fatty tissue.

In order to test this device, histotripsy cavitation was performed in ex-vivo chinchilla cerebral tissue, the results of which are shown in FIGS. 17A and 17B. In FIG. 17A, the highly specular tissue is the cerebellum granular layer, the large dark regions are the molecular layer, and within the granular layer can be seen thin dark tracts which are white matter. The ability to identify these regions using ultrasound is important for targeting specific parts of the brain.

In FIG. 17B, histotripsy ablation is in progress, where the bright circular region between 7 mm and 8 mm depth is the bubble cloud in the process of ablating. In this case, ablation is performed by driving the transducer with a 6.8 MHZ, 400 V, single-ended 10 cycle pulse train at a pulse repetition frequency (PRF) of 1000 Hz. Above the bubble cloud, a channel can be seen from the cerebellum surface down to the ablation zone, where cavitation was initiated at the surface and then plunged into the tissue. The bright streaks in the image are electronic noise from the histotripsy pulser and can be removed by synchronizing the histotripsy pulses to occur between image lines.

In FIG. 17B, ablation occurs only where targeted; however, at higher pressures it is possible that side lobes could reach cavitation pressures as well. It is important to keep these lobes below the pressure required to cavitate. Accordingly, for this device, peak pressure should be less than three times the shock scattering threshold in the treated tissue. The −3 dB radial beam width is measured at 0.116 mm and the focal length, or −3 dB axial beam width, is 0.752 mm.

The preceding examples have shown that a small, 10 mm aperture imaging and ablation device can create a histotripsy bubble cloud capable of ablating tissue with a focal zone and imaging capability allowing potentially sub-millimeter ablation accuracy. The simplicity of the present example design should facilitate the creation of multiple tools without significant cost, while the demonstration of cavitation in water at a drive voltage of 173 V suggests driving the tool directly without matching circuitry or a transformer can keep the cost of the drive electronics low as well. Side lobes on the non-co-registered device and on the co-registered device are close to −20 dB and −10 dB, respectively, suggesting that the probability of cavitation outside the focus is low. Additionally, a measured 59% one-way bandwidth allows the device to operate with a single-cycle or two-cycle pulse, maintaining a tight focus. As noted above, the present example device and the preceding example embodiments (or variations thereof) may be employed to provide an endoscopic imaging and ablation histotripsy tool.

Example 4: Effect of Intermediate Layer Acoustic Impedance on Device Performance Simulations were performed to investigate, for devices having an intermediate layer, the dependence of device performance on the acoustic impedance of the intermediate layer. Simulations were performed for devices having the same properties as in the previously described simulations, with an intermediate layer thickness of 20 microns, and with different values of the acoustic impedance of the intermediate layer. The simulations revealed that if the acoustic impedance of the intermediate layer is lower than that of both the piezoelectric layer and the acoustic lens, then a resonant increase in power is observed in the acoustic frequency spectrum.

However, if the acoustic impedance of the intermediate layer is equal to the lowest of the acoustic impedances of the acoustic lens and the piezoelectric layer, then the resonance behavior of the acoustic power spectrum with resonant peaks having increased power output is not observed. If the acoustic impedance of the intermediate layer is between that of the piezoelectric layer and acoustic lens, then a resonant increase in power is also not observed. Furthermore, if the acoustic impedance of the intermediate layer is higher than that of both the piezoelectric layer and the acoustic lens, then a slight decrease in power is observed at higher frequencies.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. An ultrasound system for generating focused ultrasound and performing histotripsy, the ultrasound system comprising:
an ultrasound transducer assembly including:
a piezoelectric layer;
an acoustic lens having a proximal surface and a curved distal surface, wherein the proximal surface is attached to the piezoelectric layer; and
an acoustic impedance matching layer coating the curved distal surface of the acoustic lens; and
driver circuitry operably connected with the ultrasound transducer assembly, wherein the driver circuitry is configured to deliver electrical pulses with a voltage and operating frequency configured to generate ultrasound pulses that produce cavitation within water;
wherein an acoustic impedance of the piezoelectric layer resides within plus or minus 40% of an acoustic impedance of the acoustic lens; and
wherein the acoustic lens has an f-number of less than two; and further
an intermediate layer is provided between the acoustic lens and the piezoelectric layer, wherein an acoustic impedance of the intermediate layer is less than the acoustic impedance of the acoustic lens and the acoustic impedance of the piezoelectric layer.

2. The ultrasound system according to claim 1 wherein the acoustic lens comprises aluminum.

3. The ultrasound system according to claim 2 wherein the acoustic lens is formed from an aluminum alloy.

4. The ultrasound system according to claim 2 wherein the acoustic lens comprises at least 85% aluminum by weight.

5. The ultrasound system according to claim 1 wherein the curved distal surface of the acoustic lens is non-spherical.

6. The ultrasound system according to claim 5 wherein the curved distal surface of the acoustic lens is elliptical.

7. The ultrasound system according to claim 1 wherein an f-number of the acoustic lens is less than unity.

8. The ultrasound system according to claim 1 wherein the acoustic impedance matching layer is formed from a polymer compatible with chemical vapor deposition.

9. The ultrasound system according to claim 1 wherein the acoustic impedance matching layer comprises an p-xylylene based polymer.

10. The ultrasound system according to claim 9 wherein the acoustic impedance matching layer comprises Parylene C.

11. The ultrasound system according to claim 1 wherein the acoustic impedance matching layer comprises polyimide.

12. The ultrasound system according to claim 1 wherein the acoustic impedance matching layer comprises a fluoropolymer.

13. The ultrasound system according to claim 1 further comprising an integrated ultrasound imaging transducer.

14. The ultrasound system according to claim 13 wherein the integrated ultrasound imaging transducer is coaxially supported relative to an axis of the acoustic lens within an aperture defined within the acoustic lens.

15. The ultrasound system according to claim 13 wherein a distal end of the integrated ultrasound imaging transducer is recessed within an aperture defined within the acoustic lens.

16. The ultrasound system according to claim 1 wherein the intermediate layer is an adhesive layer bonding the acoustic lens to the piezoelectric layer.

17. The ultrasound system according to claim 16 wherein the adhesive layer is an epoxy layer.

18. The ultrasound system according to claim 1 wherein an acoustic power spectrum thereof comprises a peak having an associated frequency that is dependent on the thickness of the intermediate layer.

19. The ultrasound system according to claim 18 wherein an intensity of the peak is also dependent on the thickness of the intermediate layer.

20. The ultrasound system according to claim 18 wherein the acoustic impedance matching layer is a quarter wave matching layer corresponding to the frequency associated with the peak in the acoustic power spectrum.

21. The ultrasound system according to claim 1 wherein the intermediate layer has a thickness between 15 and 50 microns.

22. The ultrasound system according to claim 1 wherein the intermediate layer has a thickness between 50 and 200 microns.

23. The ultrasound system according to claim 1 wherein the intermediate layer has a thickness of at least 20 microns.

24. The ultrasound system according to claim 1 wherein the intermediate layer has a thickness of at least 50 microns.

25. The ultrasound system according to claim 1 wherein a thickness of the intermediate layer is configured to effect an increase in peak emitted acoustic power in an acoustic power spectrum of the ultrasound system by a factor of at least ranging between two and three relative to an equivalent ultrasound system absent of the intermediate layer.

26. The ultrasound system according to claim 1 wherein a thickness of the intermediate layer is configured to effect an increase in peak efficiency in an acoustic efficiency spectrum of the ultrasound system by at least between 20% and 40% relative to an equivalent ultrasound system absent of the intermediate layer.

27. The ultrasound system according to claim 1 wherein the operating frequency corresponds to a frequency associated with the peak in the acoustic power spectrum.

28. The ultrasound system according to claim 1 wherein an intensity of a peak is also dependent on the thickness of the intermediate layer.

29. The ultrasound system according to claim 1 wherein the acoustic impedance matching layer is a quarter wave matching layer corresponding to a frequency associated with the peak in the acoustic power spectrum.

* * * * *